United States Patent
Grentzmann

(10) Patent No.: US 11,185,514 B2
(45) Date of Patent: Nov. 30, 2021

(54) AQUEOUS SOLUTION COMPRISING A POLYPHENOL

(71) Applicant: OPTERION Health AG, Kehrsiten (CH)

(72) Inventor: Guido Grentzmann, Hamburg (DE)

(73) Assignee: OPTERION HEALTH AG, Kehrsiten (CH)

( * ) Notice: Subject to any disclaimer, the term of this patent is extended or adjusted under 35 U.S.C. 154(b) by 0 days.

(21) Appl. No.: 16/705,860

(22) Filed: Dec. 6, 2019

(65) Prior Publication Data
US 2020/0108026 A1   Apr. 9, 2020

Related U.S. Application Data

(62) Division of application No. 15/746,110, filed as application No. PCT/EP2016/067188 on Jul. 19, 2016, now abandoned.

(30) Foreign Application Priority Data

Jul. 20, 2015  (EP) .................................... 15177541

(51) Int. Cl.
| | | |
|---|---|---|
| *A61K 31/05* | (2006.01) | |
| *A61K 47/26* | (2006.01) | |
| *A61K 47/36* | (2006.01) | |
| *A61K 9/08* | (2006.01) | |
| *A61P 13/12* | (2006.01) | |
| *A61M 1/28* | (2006.01) | |

(52) U.S. Cl.
CPC ................ *A61K 31/05* (2013.01); *A61K 9/08* (2013.01); *A61K 47/26* (2013.01); *A61K 47/36* (2013.01); *A61P 13/12* (2018.01); *A61M 1/287* (2013.01)

(58) Field of Classification Search
CPC .......... A61K 31/05; A61K 9/08; A61K 47/26; A61K 47/36; A61P 13/12; A61M 1/287
USPC ............................................ 604/29; 514/733
See application file for complete search history.

(56) References Cited

U.S. PATENT DOCUMENTS

| | | |
|---|---|---|
| 2005/0245612 A1 | 11/2005 | Blass |
| 2009/0162457 A1 | 6/2009 | Minegishi et al. |
| 2012/0045563 A1 | 2/2012 | Diguet et al. |
| 2012/0219604 A1 | 8/2012 | Kim et al. |
| 2015/0004149 A1 | 1/2015 | Burgbidge et al. |

FOREIGN PATENT DOCUMENTS

| | | |
|---|---|---|
| JP | 2005306793 A | 11/2005 |
| JP | 2014212700 A | 11/2014 |
| JP | 2015505851 A | 2/2015 |
| JP | 2015519312 A | 7/2015 |
| WO | 2013158992 A1 | 10/2013 |

OTHER PUBLICATIONS

Amri, et al.: "Administration of resveratrol: What formulation solutions to bioavailability limitations," Journal of Controlled Release, 158 (2012), pp. 182-193.
Francisco, et al.: "Improved Stability of trans-Resveratrol in Aqueous Solutions by Carboxymethylated (1,2/1,6)-β-D-Glucan," Journal of Agricultural and Food Chemistry 62 (2014), pp. 1520-1525.
Galmarini, et al.: "Stability of Individual Phenolic Compounds and Antioxidant activity during Storage of a Red Wine Powder," Food Bioprocess Technol, 6 (2013), pp. 3585-3595.
Garcia-Lopez,et al.: "Icodextrin Metabolites in Peritoneal Dialysis" Peritoneal Dialysis International, 29 (2009), pp. 370-376.
Mathew, et al., "Enzymatic synthesis of piceid glycosides by cyclodextrin glucanotransferase," Process Biochemistry, 47 (2012), pp. 528-532.
Pezzuto, et al.: "Resveratrol derivatives: a patent review (2009-2012)," Expert Opin. Ther. Patents, 23(12) 2013, pp. 1529-1546.
Rizzo, et al.: "Peritoneal adhesions in human and veterinary medicine: from pathogenesis to therapy. A review", J. Immunopharmacology and Immunotoxicology 32(3) (2010), pp. 481-494.
Romero-Perez, et al.: "Piceid, the Major Resveratrol Derivative in Grape Juices," J. Agric. Food Chem., 47 (1999), pp. 1533-1536.
Stervbo, et al., "A review of the content of the putative chemopreventive phytoalexin resveratrol in red wine," Food Chemistry, 101 (2007), pp. 449-457.
Trela and Waterhouse: "Resveratrol: Isomeric Molar Absorptivities and Stability", J. Agric. Food Chem. 44 (1996), pp. 1253-1257.
Yokoyama, et al.: "Starch Molecular Mass and Size-Exclusion Chromatogrpahy in DMSO-LiBr Coupled with Multiple Angle Laser Light Scattering," Cereal Chemistry, 75 (1998), pp. 530-535.
Silva, et al.:"Strategies to improve the solubility and stability of stilbene antioxidants: A comparative study between cyclodextrins and bile acids", J. Food Chemistry 145 (2014), pp. 115-125.
Zhang, et al.: "Enhancement of the water-solubility of resveratrol by complexation with β-cyclodextrin", Tianjin Chemical Industry, 24(4), (2010), pp. 1, 20, 21.

*Primary Examiner* — Yih-Horng Shiao
(74) *Attorney, Agent, or Firm* — Arent Fox LLP

(57) ABSTRACT

Aqueous solution, comprising, in dissolved state,—at least one stilbenoid—at least one saccharide, and method for increasing the solubility in water.

27 Claims, 8 Drawing Sheets

Results for analyte R:

| Test solution after Stirring-Time [min] | R in Medium B found [mg/L] | R in Medium E found [mg/L] | R in Medium F found [mg/L] |
|---|---|---|---|
| 5 | 6.5 | 51.3 | 5.1 |
| 10 | 12.2 | 72.1 | 5.0 |
| 18 | 14.0 | 77.2 | 8.6 |
| 24 | 12.9 | 82.1 | 10.3 |
| 30 | 16.1 | 82.6 | 12.2 |
| 45 | 15.1 | 99.9 | 11.5 |
| 60 | 14.6 | 111.3 | 10.3 |
| 12 h | 24.7 | 113.0 | 24.6 |

Description:
Rhombus Medium E
Quadrat Medium B
Triangle Medium F

| Solution | Saccharide Conc. % | R mg/L | Solub. Incr. Factor |
|---|---|---|---|
| R Ico | 0 | 6.0 | |
| R Ico | 0.024 | 10.6 | 1.8 |
| R Ico | 0.24 | 15.2 | 2.5 |
| R Ico | 2.4 | 23.8 | 4.0 |
| R Ico | 7.5 | 115.3 | 19.2 |
| R Ico | 15 | 154.1 | 25.7 |
| R Malto DE 16-19 | 0 | 6.0 | |
| R Malto DE 16-19 | 0.024 | 9.5 | 1.6 |
| R Malto DE 16-19 | 0.24 | 11.5 | 1.9 |
| R Malto DE 16-19 | 2.4 | 28.4 | 4.7 |
| R Malto DE 16-19 | 7.5 | 77.4 | 12.9 |
| R Malto DE 16-19 | 24 | 599.6 | 99.9 |
| R Malto DE 4-7 | 0 | 6.0 | |
| R Malto DE 4-7 | 0.024 | 7.7 | 1.3 |
| R Malto DE 4-7 | 0.24 | 8.7 | 1.5 |
| R Malto DE 4-7 | 2.4 | 19.6 | 3.3 |
| R Malto DE 4-7 | 7.5 | 21.2 | 3.5 |
| R Malto DE 4-7 | 24 | 160.3 | 26.7 |

| Solution | Sacch % | R mg/L |
|---|---|---|
| Polydatin Malto DE 16-19 | 0 | 155.8 |
| Polydatin Malto DE 16-19 | 0.024 | 163.4 |
| Polydatin Malto DE 16-19 | 0.24 | 179.6 |
| Polydatin Malto DE 16-19 | 2.4 | 222.3 |
| Polydatin Malto DE 16-19 | 7.5 | 333.2 |
| Polydatin Malto DE 16-19 | 24 | 504.4 |
| Pterostilben Malto DE16-19 | 0 | 2.9 |
| Pterostilben Malto DE16-19 | 0.024 | 3.0 |
| Pterostilben Malto DE16-19 | 0.24 | 3.0 |
| Pterostilben Malto DE16-19 | 2.4 | 3.0 |
| Pterostilben Malto DE16-19 | 7.5 | 9.0 |
| Pterostilben Malto DE16-19 | 24 | 341.3 |

AQUEOUS SOLUTION COMPRISING A POLYPHENOL

This application is a division of U.S. patent application Ser. No. 15/746,110 filed Jan. 19, 2018, pending, which is a § 371 of PCT/EP2016/067188 filed Jul. 19, 2016, and claims priority under Section 119 from European Patent Application No. EP 15 177 541.8 filed on Jul. 20, 2015, each of which is hereby incorporated by reference in its entirety.

The present invention relates to an aqueous solution comprising a stilbenoid and to a method for increasing the solubility of stilbenoids in aqueous environment.

BACKGROUND OF THE INVENTION

Stilbenoids have been suggested as treatment and prevention against several diseases, including diabetes, cancer, inflammation and degenerative diseases. However, many stilbenoids remain difficult to be employed clinically, as well as food additives, because of low aqueous solubility. Various approaches like nanosizing, self-microemulsifying drug delivery systems (SMEDDS), microencapsulation, complexation, and solid dispersion can be used to increase the bioavailability of stilbenoids. Other possibilities lie in synthesis of stilbenoid derivatives with higher aqueous solubility. Solubility can be measured, at a given temperature, in different ways, as absolute solubility or as solubility within a limited time of stirring (e.g. one hour at room temperature). The latter is an important measure in terms of industrial application of a given solute.

A further aspect of stilbenoids is that many of them are rather instable. Increased solubility may also result in increased stability of stilbenoids.

Stabilization of stilbenoids in solution can be obtained by adapting pH. Stabilization of resveratrol has previously been described at pH 1 (Trela et al., J. Agric. Food Chem. 1996, 44, 1253-1257). However, such acidic pH are not desired for many applications.

The task of the present invention was to provide with a technical solution to overcome one or more of the above-mentioned problems.

SUMMARY OF THE INVENTION

The present invention provides with an aqueous solution and a method as defined in the claims and in the following description.

The invention provides with an aqueous solution, comprising, in dissolved state,
  at least one stilbenoid,
  at least one saccharide.

The molecular weight of the saccharide may be up to 1000 kD, preferably up to 500 kD, more preferably up to 50 kD. 1 D (Dalton) corresponds to 1 g/mol.

More preferably, the molecular weight is in a range of 90 D to 1000 kD, preferably 90 D to 500 kD, more preferably 90 D-50 kD. Said molecular weight is range of a molecular weight of molecules present in the saccharide. The saccharide can be a mixture of saccharide-molecules of different chain lengths (different numbers of monosaccharide units).

An aqueous solution is intended to mean a solution that is based on water as the sole or the main solvent. Water as the main solvent means that the proportion of water in the total mass of solvents is ≥60% by volume, preferably ≥70% by volume, or ≥80% by volume, most preferably ≥90% by volume. Co-solvents that are miscible with water may be present.

DETAILED DESCRIPTION

In one embodiment, the stilbenoid may be resveratrol (trans-3,5,4'-trihydroxystilbene, a resveratrol derivative, dihydro-resveratrol, piceatannol, pterostilbene, or piceid (resveratrol-3-O-β-mono-D-glucoside, also named as trans-3,5,4'-trihydroxystilbene-3-O-β-D-glucopyranoside).

A stilbenoid may be chosen from a structure of the formula 100,

Formula 100:

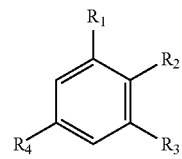

wherein $R_4$ is

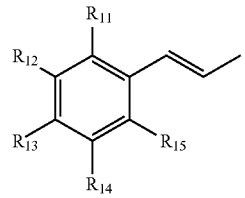

wherein $R_1$, $R_2$, $R_3$, $R_{11}$, $R_{12}$, $R_{13}$, $R_{14}$, and $R_{15}$ may be
—H, —OH, —O—$R_{Alk}$, —CHO, —$CR_{Ak}$O, —COOH,
—COO—$R_{Alk}$, —CO—NH—$C_nH_{2n}$—COOH, —CO—NH—$C_nH_{2n}$—COO$^-$,
—CN, —Cl, —Br, —I, —$NO_2$,
—$C_nH_{2n}$CN, —$C_nH_{2n}$—Cl, —$C_nH_{2n}$—Br, —$C_nH_{2n}$—I, —$C_nH_{2n}$—$No_2$,
—O—$PO_3^{2-}$, —O—$PO_3H$; —O—$PO_3H_2$, —NH2, —$NHR_{Alk}$, —$NR_{Alk1}R_{Alk2}$, —$N^+H3$, —$N^+H2R_{Alk}$, —$N^+HR_{Alk1}R_{Alk2}$, —$N^+R_{Alk2}R_{Alk3}$,
—CN, —$B(OH)_2$, —OCHO, —O—$CR_{Alk}$O, —$OCF_3$, —O—CN, —$OCH_2CN$,
or one of the following moieties:

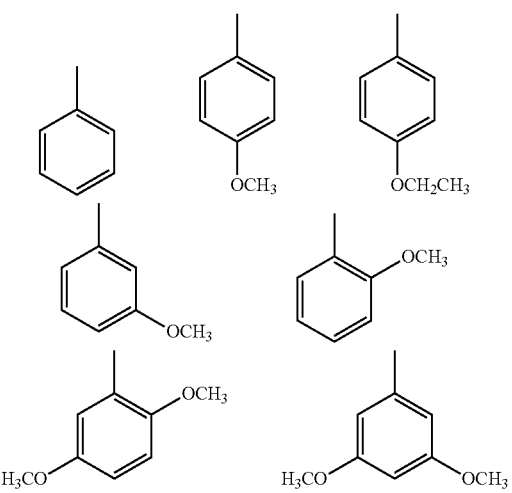

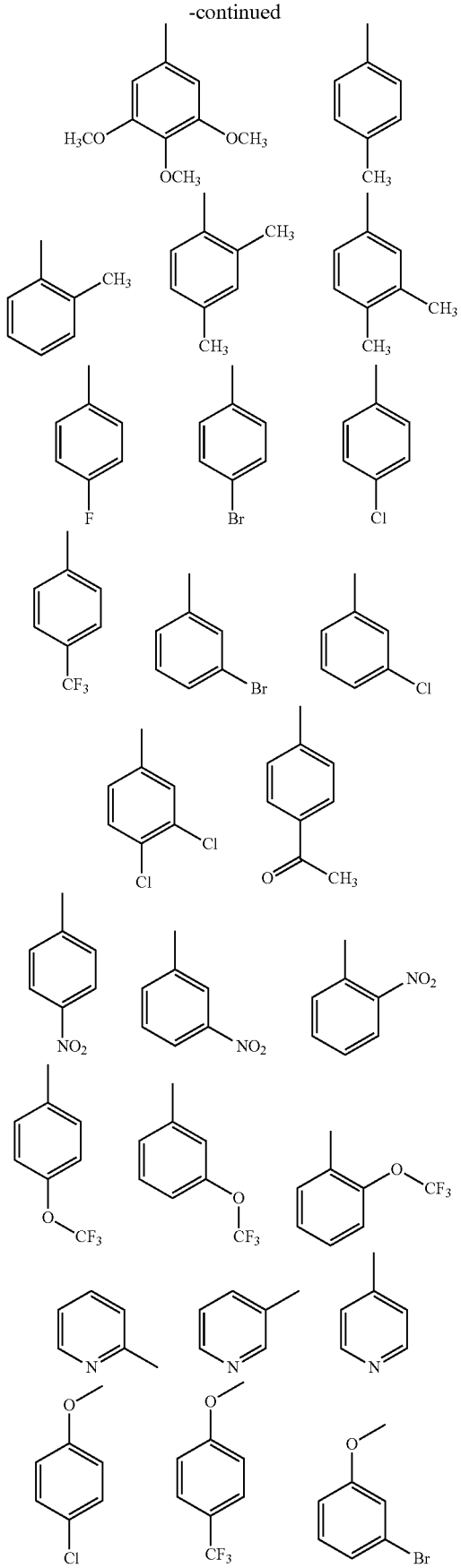
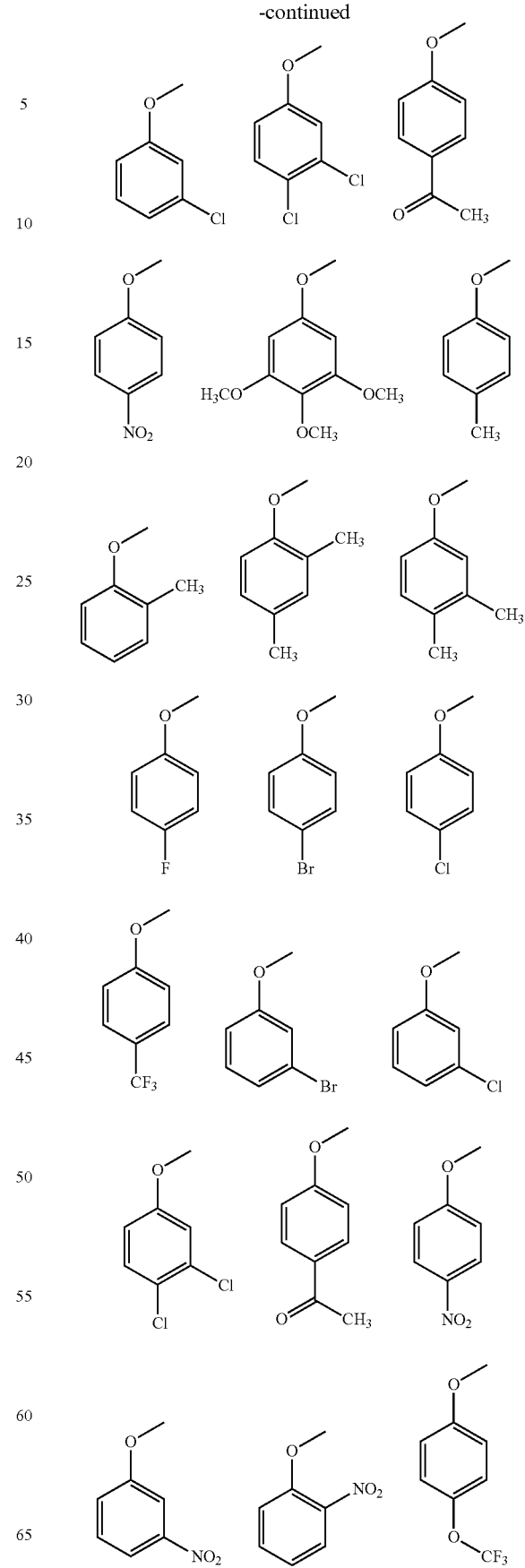

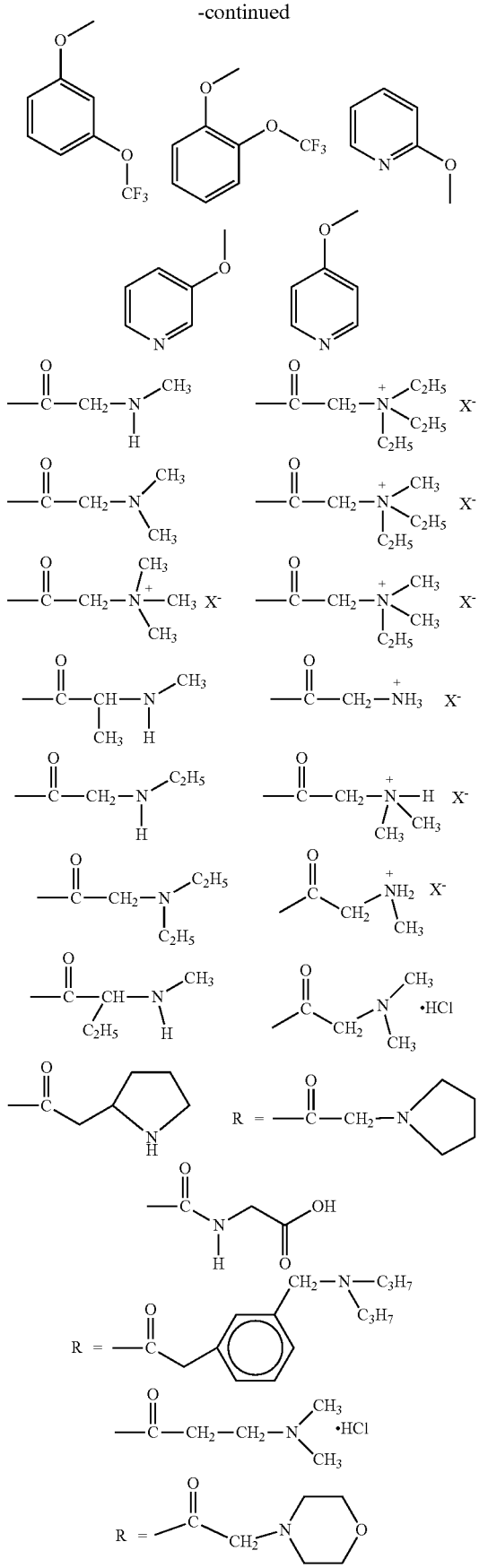
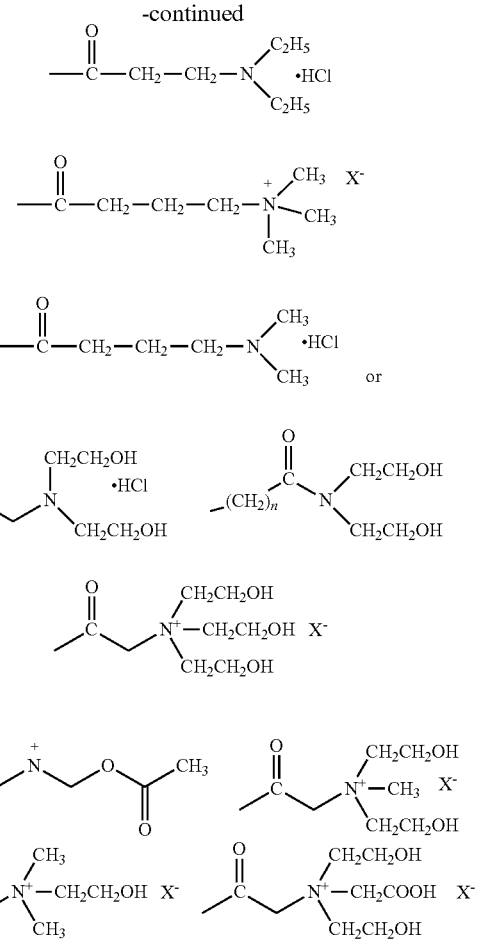

and/or where $R_{ak}$, $R_{alk1}$ and $R_{alk2}$ may be $CH_3$, $C_2H_5$, $C_3H_7$ or $C_4H_9$, and/or where $C_nH_2n$ may be $CH_2$, $C_2H_4$, $C_3H_6$, $C_4H_8$, and/or where R11, R12, R13, R14 or R15 may be a mono or oligo saccharide.

and/or where $X^-$ may be a free soluble cation, with the proviso that at least one of $R_1$, $R_2$, $R_3$, $R_{11}$, $R_{12}$, $R_{13}$, $R_{14}$, and $R_{15}$, preferably at least two thereof, is a hydroxyl group.

Resveratrol derivatives are for example described in John M Pezzuto et al., Resveratrol derivatives: a patent review (2009-2012), Expert Opin. Ther. Patents (2013) 23(12). The resveratrol derivative may be selected from following compounds:

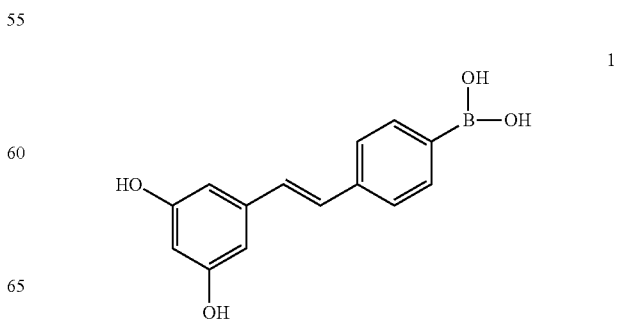

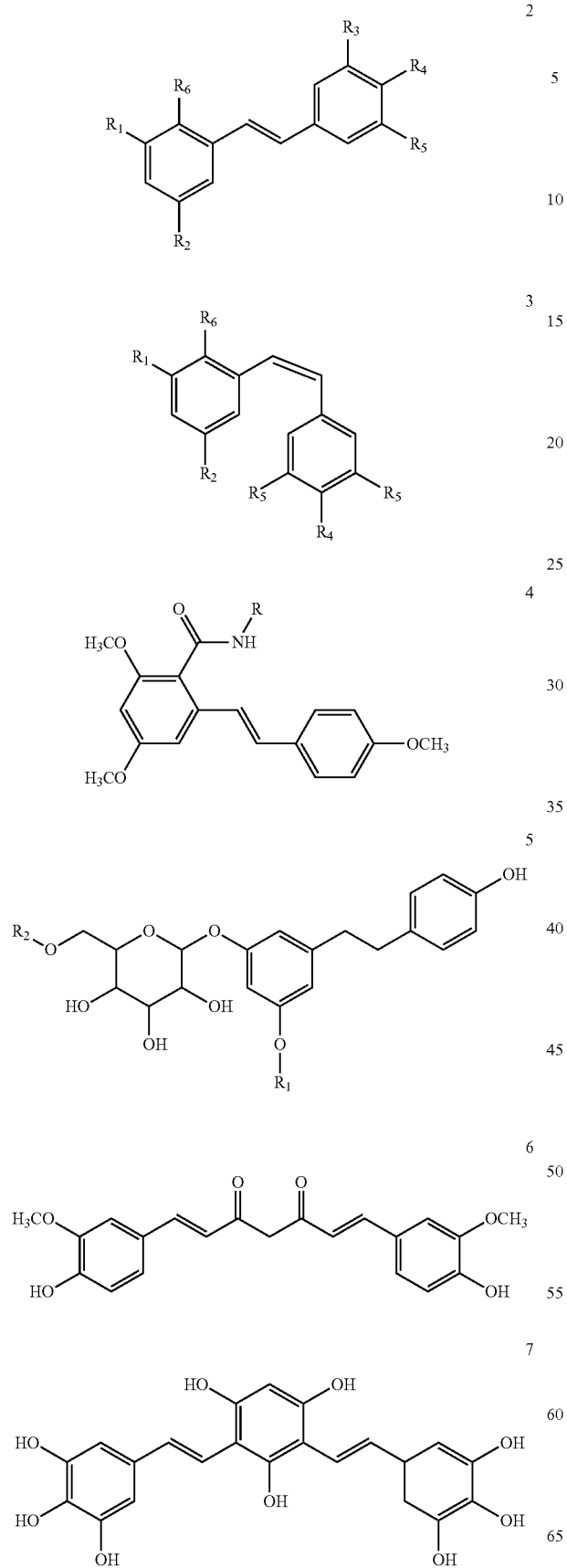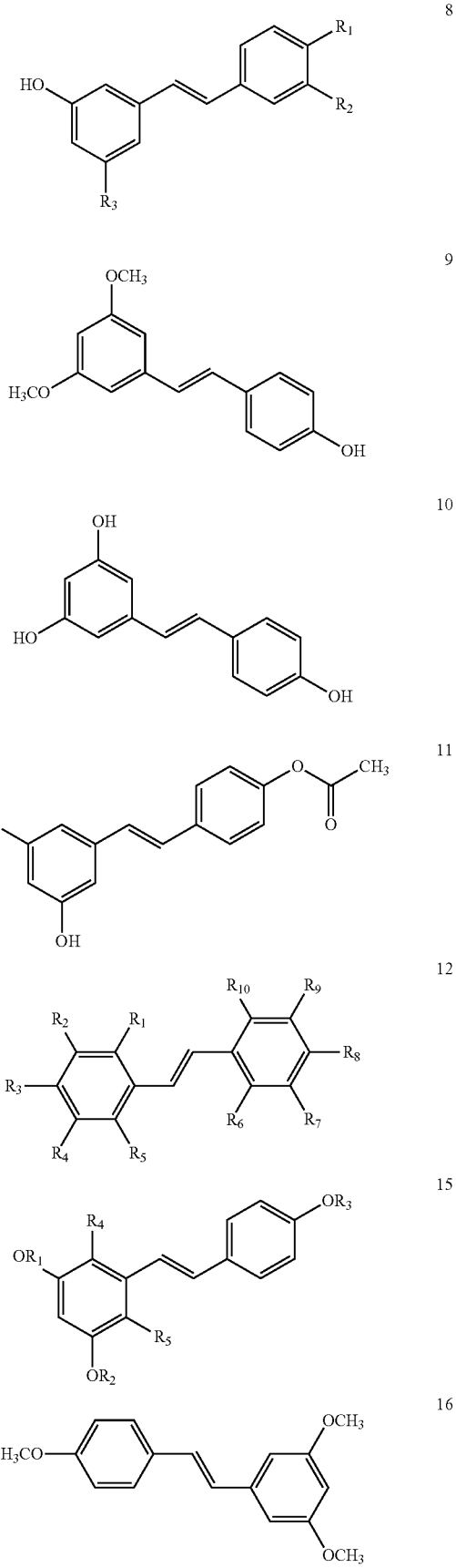

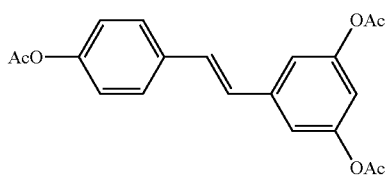

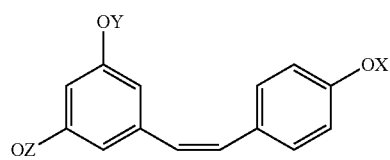

wherein in compound 2 and compound 3
R1=R2=R4=OH, R3=R5=R6=H; or
R1=R2=R4=OCH3, R3=R5=R6=H; or
R1=R2=R4=OCH3, R3=R5=H; R6=OH; or
R1=R2=R3=R5=OCH3, R4=R6=H; or
R1=R2=R3=R5=OCH3, R4=H, R6=OH; or
R1=R2=R3=R4=OCH3, R5=R6=H; or
R1=R2=R3=R4=OCH3, R5=H, R6=OH.

wherein in compound 4 R is one of the following moieties:

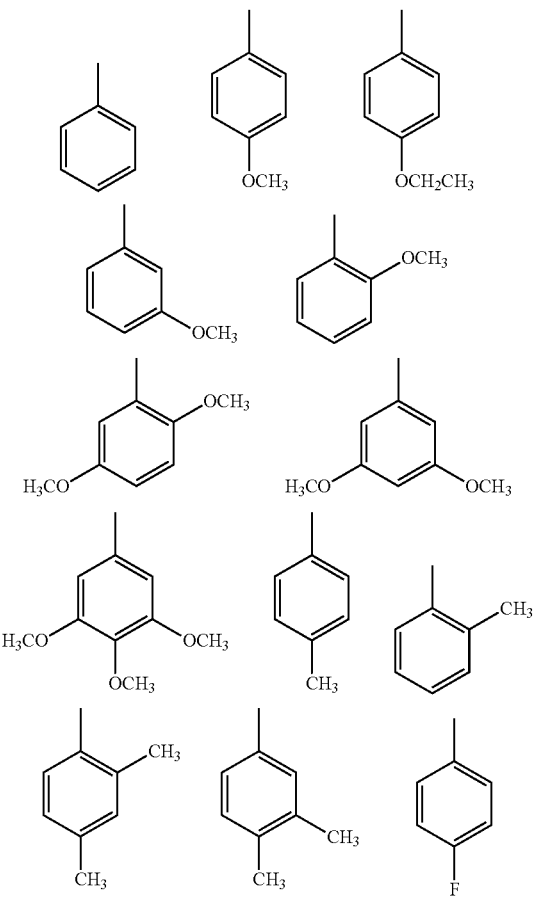

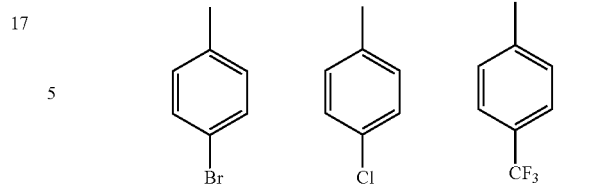

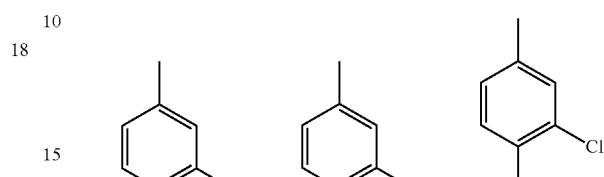

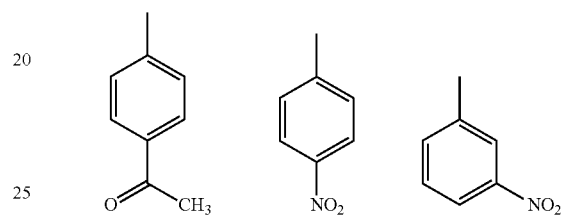

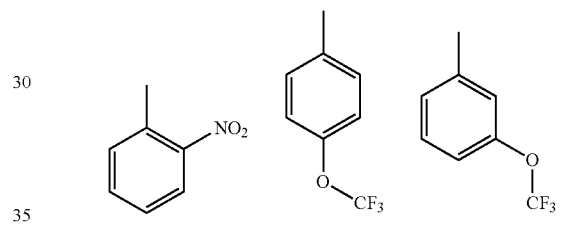

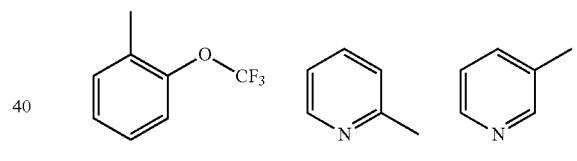

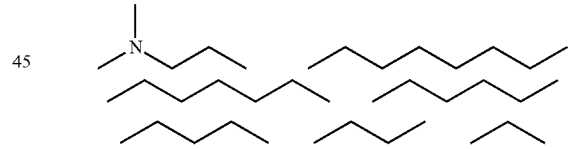

wherein in compound 5
R₁ is hydrogen or a group of formula

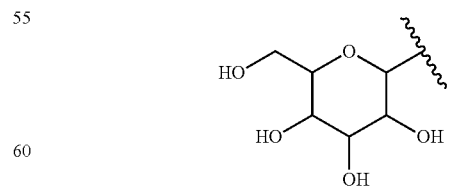

R2 is hydrogen or forms together with the oxygen to which it is bound an acyl group (—OOO—R3), wherein R3 is a C1-C22 alkyl group or a C2-C22 alkenyl group, wherein, if R2 is hydrogen R1 forms a group of above-shown formula, wherein in compound 6, R is one of the following moieties:
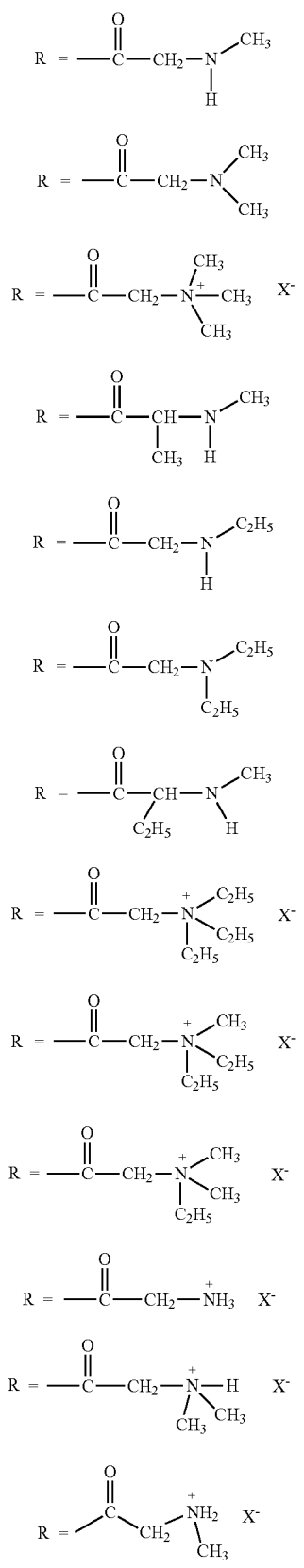
(1) (2) (3) (4) (5) (6) (7) (8) (9) (10) (11) (12) (13)
-continued
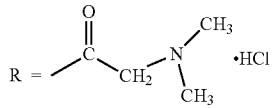
(14)
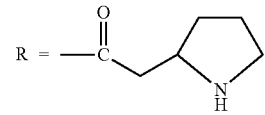
(15)
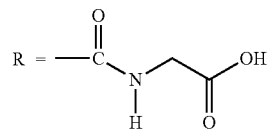
(16)
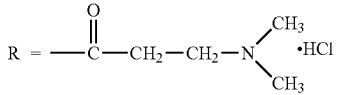
(17)
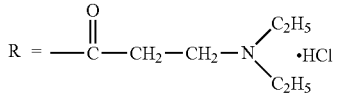
(18)
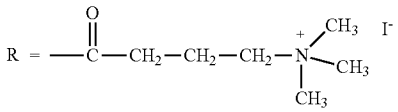
(19)
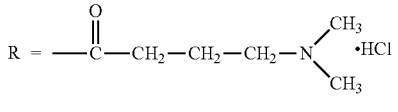
(20)
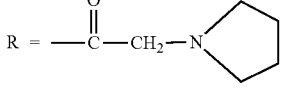
(21)
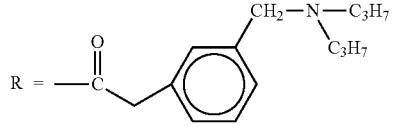
(22)
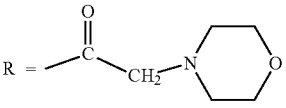
(23)
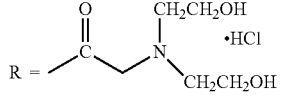
(24)
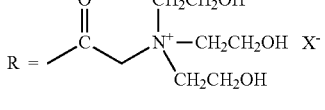
(25)
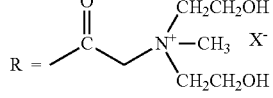
(26)

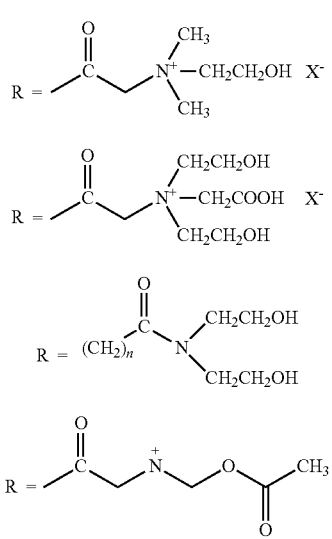

wherein in compound 8
R1=OCH3, R2=OH, R3=O-Glucose; or
R1=OCH3, R2=H, R3=O-Glucose; or
R1=OCH3, R2=OH, R3=OH; or
R1=OCH3, R2=H, R3=OH; or
R1=OH, R2=OH, R3=O-Glucose; or
R1=OH, R2=OH, R3=OH;
wherein in compound 12
R1, R2, R3, R4, R5, R6, R7, R8, R9, and R10 are independently chosen from hydrogen, hydroxyl, hydrocarbyl, substituted hydrocarbyl, hydrocarbyloxy, substituted hydrocarbyloxy, and sulfoxy; provided that at least one of the R groups is a hydroxyl or substituted hydroxyl group; and provided that if compound 12 is monomeric, then compound 12 is other than resveratrol,
wherein in compound 15
R1, R2 and R3, independently from one another, represent H or (C1-C3)alkyl; R4 and R5 are identical or different and represent hydrogen, linear or branched (C1-C5)alkyl, a prenyl group —CH2-CH=C(CH3)2, a geranyl group —CH2-CH=C(CH3)(CH2)2CH=C(CH3)2
or R4 and R1, and independently R5 and R2, together with the atoms they are linked to, form one of the following groups:

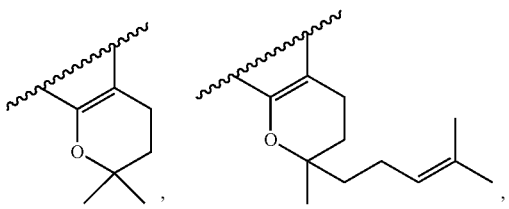

with the provisos that R4 and R5 are not both hydrogen and that when R1=R2=R3=H, R4 and R5 are not a prenyl group and hydrogen, respectively,
wherein in compound 18 X, Y, and Z are either hydrogen or a protective group, provided that at least one of X, Y, and Z is the protective group.

In one embodiment of the aqueous solution the saccharide is a monosaccharide, a disaccharide, an oligosaccharide, a polysaccharide, or a mixture of different mono-, di-, oligo- and/or poly-saccharides. A polysaccharide preferably comprises, or is composed of, up to 2500 monosaccharide units, preferably up to 500 monosaccharide units in maximum.

A mono-saccharide may be selected from a triose such as glyceraldehyde and glucerone, a tetrose, such as erythroses, threose and erythrulose, a pentose, such as ribose, arabinose, xylose, lyxose, ribulose and xylulose, or a hexose, such as allose, altrose, glucose, mannose, gulose, idose, galactose, talose, psicose, fructose, sorbose and tagatose, and may also be defined as a saccharide of a molecular weight of roughly 90 to 200 D.

The term saccharide may comprise derivatives of monosaccharide, such as aminoglycosides, such as glucosamine, galactosamine, N-acetylglucosamine, N-acetylgalactosamine, which may not or may be sulfated to different degrees.

A mono-saccharide may be further selected from uronic sugars, such as glucuronic acid or iduronic acid.

A di-saccharide may be selected from the reducing α-Glucanes trehalose, Kojibiose, Nigerose, maltose and Isomaltose or other di-saccharides such as sucrose, lactulose, lactose, cellobiose, chitbiose, β, β-Trehalose, α,β-Trehalose, Sophorose, Laminaribiose, Gentiobiose, Turanose, Maltulose, Palatinose, Gentiobiulose, Mannobiose, Melibiose, Melibiulose, Rutinose, Rutinulose, Xylobiose, and may also be defined as a saccharide of a molecular weight of 150 to 400 D.

The term di-saccharide may further comprise glycosaminoglycan-di-saccharides", composed of an aminoglucoside and a monosaccharide, which may be acetylated or sulfated to different degrees.

An oligo-saccharide may be a trisaccharide or saccharides of higher degree of polymerization, selected from an oligomer of above cited saccharides, a product of limited hydrolysis of a linear or branched homo-polysaccharide, such as a amylose, amylopectin, fructan such as inulin, glucan, galactan and mannan, cellulose, arabic gum, amylose, amylopectin, glycogen, dextran, and hemicellulose, a product of limited hydrolysis of a hetero-polysaccharide, such as hemi-cellulose, arabinoxylose, or pectine, or a product of limited hydrolysis of a mixed polysaccharide, such as starch.

In one embodiment, the saccharide is a glucan. The glucan may be a linear or a branched glucan.

The glucan may be selected from sucrose, maltose, maltotriose, isomaltotriose, maltoteraose, trehalose, kojibiose, nigerose, isomaltose, β,β-Trehalose, α,β-Trehalose, gentiobiose, melibiose, maltodextrin, icodextrin, an oligomer that can be obtained by limited hydrolysis of a linear or branched glucan, such as starch, amylose, amylopectin, amylose, amylopectin, glycogen, dextran, or an oligomer that can be obtained by limited hydrolysis of Pullulan.

In a further, more specific embodiment, the saccharide is a reducing alpha-glucan.

The reducing alpha-glucan may be selected from maltose, maltotriose, isomaltotriose, maltotetraose, maltodextrin, icodextrin, an oligomer that can be obtained by limited hydrolysis of a linear or branched glucan, such as starch, amylose, amylopectin, amylose, amylopectin, glycogen, dextran, or an oligomer that can be obtained by limited hydrolysis of Pullulan.

Further glucans are exemplified by, but not limited to, isomaltotriose, nigerotriose, maltotriose, melezitose; maltotriulose, raffinose, kestose, maltodextrins, preferably of different molecular weight, or other hydrolysis products from alpha glucans, such as dextran, glycogen, pullulan, floridean starch, and starches, such as amylose and amylopectine, and mixtures thereof, preferably with molecular weights between 300 D and 300 KD.

Maltodextrin may be defined as a mixture of saccharides with a DE (dextrose equivalent) between 3 and 20, preferably presenting more than 95% α1-4 bonds and less than 5% α1-6 bonds.

One Example for maltodextrin may be Maltodextrin with a DE(dextrose equvalent) of 16-19.

Another example for maltodextrin may be Maltodextrin with a DE of 4 to 6.

Dextrans may be defined as a mixture of glucose-oligomers composed of straight chains by α-1,6 linkages, which may be branched at α-1,3 linkages.

One example for dextran may be dextran of 2.5 to 4 kD weight average molecular weight.

A further example for dextran may be Dextran of 4 to 16 kD, preferably 8 to 12 kD, more preferably about 10 kD weight average molecular weight;

A further example for Dextran may be Dextran with an weight average molecular weight of 40 to 100 kD, preferably 50-90 kD, more preferably 60 to 80 kD.

An example for a hydrolysate of a reducing alpha glucan hydrolysate may be Glycogen with a weight average molecular weight of 80 to 120 kD.

Another example for a hydrolysate of a reducing alpha Glucan may be pullulan with a weight average molecular weight of 100 to 200 kD.

Average molecular weight is preferably measured in connection with the present invention by the method of "gel permeation chromatography with light scattering and refractive index detection (GPC-RI-MALLS system)".

Dextrose equivalent (DE) is a measure of the amount of reducing sugars present in a sugar product, relative to dextrose (a.k.a. glucose), expressed as a percentage on a dry basis. For example, a maltodextrin with a DE of 10 would have 10% of the reducing power of dextrose (which has a DE of 100) (https://en.wikipedia.org/wiki/Dextrose_equivalent).

Polysaccharide hydrolysates, such as hydrolysates of glucans, preferably reducing alpha glucans, such as starch, amylose, amylopectin, amylose, amylopectin, glycogen, dextran, or Pullulan can be obtained by limited hydrolysis of such poly-saccharides.

An oligo-saccharide may be selected from an oligomer of above cited saccharides, a product of limited hydrolysis of a linear or branched homo-polysaccharide, such as a amylose, amylopectin, fructan such as inulin, glucan, galactan and mannan, cellulose, arabic gum, amylose, amylopectin, glycogen, dextran, and hemicellulose, a product of limited hydrolysis of a hetero-polysaccharide, such as hemi-cellulose, arabinoxylose, or pectin, or a product of limited hydrolysis of a mixed polysaccharide, such as starch.

The term "saccharide" also comprises derivatives of a saccharide. So, the saccharide may be a derivative of a saccharide, such as an oxidized saccharide, such as a saccharic acid, or another acidic saccharide, such as a sulfuric ester groups containing saccharide, a deoxy-saccharide, an acetylated saccharide or an amylated saccharide, and corresponding homo- and hetero-oligo-saccharides. Other derivatives of saccharides are anoxidized saccharide, such as a saccharic acid, or another acidic saccharide, such as a sulfuric ester groups containing saccharide, a deoxy-saccharide, an acetylated saccharide or an amylated saccharide, and corresponding homo- and hetero-oligo-saccharides.

In one embodiment, the saccharide is selected from glucose, fructose, sucrose, maltose, a homo-oligomer/polymer thereof, a hetero-oligomer/polymer thereof, or a mixture thereof.

In another embodiment the saccharide is selected from glucose, icodextrin, or a mixture thereof.

Different concentrations of the at least one saccharide may be employed. If more than one saccharide, i.e. more than one type of saccharide, is present, the concentration refers to the total concentration of all saccharides present in the solution.

If in this description concentrations are given in percent by weight, 1% by weight corresponds to 10 g/L.

The at least one saccharide may be present in a total concentration of ≥02% by weight (200 mg/L). It has been shown that a concentration as low as this concentration enhances stilbenoid stability.

The at least one saccharide may be present in a total concentration of ≥75% by weight (7.5 g/L). It has been shown that such concentration enhances stilbenoid stability and/or solubility of stilbenoid.

The at least one saccharide may be present in a total concentration of % by weight. It has been shown that such concentration further enhances stilbenoid stability and/or solubility of stilbenoid.

The at least one saccharide may be present in a total concentration of ≥5% by weight. It has been shown that such concentration further enhances stilbenoid stability and/or solubility of stilbenoid.

The at least one saccharide may be present in a total concentration of ≥7.5% by weight (75 g/L). It has been shown that such concentration enhances stilbenoid stability and solubility of stilbenoid.

The at least one saccharide may be present in a total concentration of ≥20% by weight (200 g/L). It has been shown that such concentration further enhances stilbenoid stability and solubility of stilbenoid.

The upper limit of concentration of the at least one saccharide is preferably the concentration of saturation. Another possible upper limits, that could be combined with any of the lower limits in this description, are 45%, 40%, 30% by weight.

The molecular weight of oligo- or poly-saccharides varies widely:

For example as food additives oligo-saccharides are commonly applied at sizes between 1 and 20 KD, which however does not limit the invention.

Icodextrin, which is a type of maltodextrin or can be derived from maltodextrin, is a polydisperse mixture of polymers with varying chain lengths (2-300 linked glucose molecules corresponding to molecular weights of 350 to 50 kD), its molecular weight is characterized by both a number average (Mn) and a weight average (Mw) molecular weight. The number average molecular weight Mn for icodextrin, ranges from 5000 to 6500 Da and the weight average molecular weight Mw ranges from 13 000 to 19000 Da (Garcia-Lopez et al., Peritoneal Dialysis International, Vol. 29, p 370).

In the frame of this application oligo-saccharides and polysaccharides cover saccharides composed of between 3 and 5000 monosaccharide-units, preferably 3 and 500 monosaccharide-units, more preferably 3 to 300 monosaccharide-units.

In another definition, oligo-saccharides and polysaccharides have a molecular weight between 250 D and 1000 kD, preferably 250 D and 50 KD.

Preferably, an oligosaccharide means saccharides composed of between 3 to 20 monosaccharide-units. Preferably, a polysaccharide means saccharides composed of between 21 to 5000 monosaccharide-units.

The term "between" is intended to include the lower and upper limit of the respective range, if not otherwise indicated. So, is a range is disclosed as "between X and Y", X and Y are included.

Molecular weight of polysaccharides is very heterogeneous. For example, the Mw (Berry method) of starch from waxy corn is $2.27 \times 10(8)$ Da, waxy rice $8.9 \times 10(7)$ Da, cassava $5.7 \times 10(7)$ Da, Hylon V $2.7 \times 10(7)$ Da, Hylon VII $4.8 \times 10(6)$ Da, and potato amylose $1.9 \times 10(5)$ Da (Yokoyama et al., Cereal chemistry, volume: 75, 530.

In certain applications, such as "power-drinks" artificial poly-saccharides of a size of up to 700 KD are advertised.

In one embodiment, the at least one saccharide has a molecular weight of 90 D to 500 D. (1 D=1 g/mol). This molecular weight range can be combined with each concentration given in this description.

In a more specific embodiment, the at least one saccharide of a molecular weight of 90 D to 500 D and is present in a total concentration of 4.02% (200 mg/L) minimum, thereby enhancing stilbenoids solubility and/or stability.

In a more specific embodiment, the at least one saccharide of a molecular weight of 90 D to 500 D is present in a total concentration of 4.75% (7.5 g/L) minimum, thereby enhancing stilbenoids solubility and/or stability.

In a further specific embodiment, the at least one saccharide of a molecular weight of 90 D to 500 D is present in a total concentration of ≥7.5% (75 g/L) minimum, thereby enhancing stilbenoids solubility and stability.

In another embodiment, the at least one saccharide has a molecular weight of 350 D to 50 kD.

In a more specific embodiment the at least one saccharide of a molecular weight of 350 kD to 1000 kD, preferably 350 D to 50 kD is present in a total concentration of 4.02% by weight (200 mg/L), thereby minimum enhancing stilbenoid solubility and/or stability.

In a further specific embodiment, at least one saccharide of a molecular weight of 350 D to 1000 kD, preferably 350 D to 50 kD is present in a total concentration of 4.2% by weight (2 g/L), thereby enhancing stilbenoid solubility and/or stability.

In a further specific embodiment, at least one saccharide of a molecular weight of 350 D to 1000 kD, preferably 350 D to 50 kD is present in a total concentration of ≥2% by weight (20 g/L), thereby enhancing stilbenoid solubility and/or stability.

In a further specific embodiment, at least one saccharide of a molecular weight of 350 D to 1000 kD, preferably 350 D to 50 kD is present in a total concentration of ≥5% by weight (50 g/L), thereby enhancing stilbenoid solubility and/or stability.

In a further specific embodiment, at least one saccharide of a molecular weight of 350 D to 1000 kD, preferably 350 kD to 50 kD is present in a total concentration of ≥7.5% by weight (75 g/L), thereby enhancing stilbenoid solubility and/or stability.

Following embodiments are related to stilbenoid concentrations. It is to be understood that any stilbenoid concentration (or concentration range) mentioned in this description can be combined with any saccharide concentration (or concentration range) mentioned in this description.

In one embodiment of the invention, the at least one stilbenoid is present in a total concentration of 0.1 mg/L-40 mg/L.

In one embodiment of the invention, the at least one stilbenoid is present in a total concentration of ≥0.15 mg/L.

In one embodiment of the invention the at least one stilbenoid is present in a total concentration of ≥1.5 mg/L.

In one embodiment of the invention the at least one stilbenoid is present in a total concentration of ≥15 mg/L.

In one embodiment of the invention the at least one stilbenoid is present in a total concentration of 0.1 mg/L to 100 mg/L. It has been shown that with such concentration increased biocompatibility can be reached. Such concentration is particularly suitable for medical applications.

In one embodiment of the invention the at least one stilbenoid is present in a total concentration of 10 mg/L-1600 mg/L. It has been shown that such concentration allows treatment of acute medical conditions. Such concentration is particularly suitable for medical applications.

In one embodiment of the invention the at least one stilbenoid is present in a total concentration of 10 mg/L—saturation. Such concentration is particularly suitable for food additives or stocksolutions.

The at least one stilbenoid may be present in a concentration of 0.001 mg/L to 5 g/L, preferentially between 0.001 mg and 1 g/l further preferred between 0.01 and 500 mg/L. These concentrations, and other concentrations for stilbenoid that are given in g/L, relate to the total concentration of all stilbenoids if more than one stilbenoid is present.

Particularly in case of medical application, stilbenoid concentration of the final application may be adapted to different purposes. To enhance biocompatibility of a water based application, such as decrease of local cyto-toxic or inflammatory stress, concentrations between 0.01 mg/L and 500 mg/L are preferred.

Particularly in case that the application is supposed to act to systemically deliver stilbenoids, to treat systemic and/or acute conditions: diabetes, inflammatory diseases such as cardiovascular diseases, COPD, rheumatoid arthritis, digestive tract inflammatory diseases such as gastritis and IBD, dermal inflammatory diseases such as dermatitis, auto-inflammatory diseases such as Lupus, different kinds of primary and/or secondary cancers, degenerative diseases such as neurodegenerative diseases such as Parkinson's Alzheimer's and Huntington's or sclerotic neurodegenerative diseases, fibrosis such as cystic fibrosis or organ functional decrease such as decrease of residual renal activity, a higher range of stilbenoid concentrations such as between 0.1 mg up to 5 grams per Liter are preferred.

This does not exclude that even lower concentrations between 0.01 mg/L and 500 mg/L may very well exhibit such beneficial effect against described systemic or acute conditions.

The term "between" is intended to include the lower and upper limit of the respective range, if not otherwise indicated. So, is a range is disclosed as "between X and Y", X and Y are included.

The at least one stilbenoid may be present in a concentration of 0.02 µM to 315 µM, preferentially 0.07 µM to 100 µM further preferred 0.2 µM to 50 µM. Said molar concentration relates to each individual stilbenoid if more than one stilbenoid is present (M=Mol/L).

In further embodiments, the stilbenoid be present in a concentration of 0.05 to 60 µM, preferentially between 0.05 to 40 µM further preferred between 0.05 to 20 µM. These concentrations, and other concentrations for stilbenoid that are given in µM, relate to the total concentration of all stilbenoids if more than one stilbenoid is present.

In still further embodiments, the stilbenoid may be present in a concentration of 0.001 mg/L to 5 g/L, preferentially between 0.001 mg/L and 1 g/l further preferred between 0.01 and 500 mg/L. These concentrations, and other concentrations for stilbenoid that are given in g/L, relate to the total concentration of all stilbenoids if more than one stilbenoid is present.

The upper limit of concentration of the at least one stilbenoid is preferably the concentration of saturation. Another possible upper limits, that could be combined with any of the lower limits in this description, are 1600 mg/L, or 1200 mg/L The concentration of saccharide may be 0.025% until saturating concentration of the particular saccharide in an aqueous solution.

In another embodiment, the concentration of the saccharide may be 0.05-50% by weight (of the total solution), preferably 0.24-24 by weight, even more preferably 0.5-15% by weight.

In another embodiments, the concentration of the saccharide may be 15-50% by weight (of the total solution), preferably 24-50% by weight.

In another embodiments, the concentration of the saccharide may be 4.0-50% by weight (of the total solution), preferably 4.0-24% by weight, more preferably 7.0-15% by weight.

In another embodiments, the concentration of the saccharide may be 2.0-50% by weight (of the total solution), preferably 2.0-24% by weight, more preferably 2.0-15% by weight, even more preferably 2.0-7% by weight.

In another embodiments, the concentration of the saccharide may be 0.05-24% by weight (of the total solution), 0.2-15% by weight, 0.5-7% by weight, or 0.5-2% by weight In one embodiment, the aqueous solution of the invention has a physiologically neutral pH between 6 and 8, preferably 6.8-7.5. It has been shown that stilbenoid could be stabilized in an aqueous solution of the invention even at such pH.

In one embodiment, the aqueous solution of the invention has an acidic pH between 1 and 6. Such pH is suitable to further stabilize stilbenoid. We, however, show that a pH of 3 to 3.5 significantly stabilize stilbenoids, particularly the stilbenes resveratrol and piceid. This is of importance because it allows solubilization of stilbenoid in acidified glucose solutions, such as commonly applied in many peritoneal dialysis solutions. We further show that ph 3 adjusted Extraneal® solution sufficiently stabilize resveratrol to allow heat sterilization of such a solution, without degradation of the stilbenoid.

In a further aspect, the present invention is directed to a method for increasing the solubility of a stilbenoid in water, comprising:
dissolving at least one saccharide in the water,
dissolving the stilbenoid in the water.

For the method of the invention, it is explicitly referred to the above and below disclosure, particularly to saccharides, stilbenoids, concentrations, molecular weights and pH. All features mentioned above and elsewhere in this description could be employed in the method.

Further explantions and embodiments of the present invention are provided hereunder.

The present invention relates to solutions consisting of as well as comprising water, stilbenoids, and mono-, di-, oligo- and/or polysaccharides, particularly nutritional and/or biologically inactive mono-, oligo- or polysaccharides.

The invention relates to the use of said saccharides for solubilization and stabilization of Stilbenoids into water based foods and medical applications. Solutions may further contain one or several pH buffer and other solutes.

In the present invention, it has been shown that solubility of stilbenoids may also be increased by amino acids. So, the present invention also describes an aqueous solution, comprising, in dissolved state,
at least one stilbenoid,
at least one amino acid.

Amino acids can also be added as a further component to a solution comprising a stilbenoide and a saccharide, which was described before.

One or more amino acids may be present individually or as mixtures at concentrations between 0.01 and 10% for therapeutic liquids, or at higher concentrations, if highly concentrated solutions shall be formulated.

Emphasis is drawn to the fact that this invention does not describe compositions such as emulsions, suspensions, dispersions, complexations or chelations of stilbenoids, but simply the increased aqueous solubility of stilbenoids by addition of mono-, di-, oligo- and/or poly-saccharides.

Stilbenoids are substances, particularly polyphenols, particularly naturally occurring polyphenols, corresponding to the structure C6-C2-C6 (Stilbene) as basic structure, and belonging to the family of phenylpropanoids. Well studied Stilbenes are resveratrol (trans-3,5,4'-trihydroxystilbene), pinosylvine, piceatannol, pterostilbene, and a glycoside, piceid (resveratrol-3-O-β-mono-D-glucoside, also named as trans-3,5,4'-trihydroxystilbene-3-O-β-D-glucopyranoside).

The solution of the invention may further comprise salts and other components to establish physiological conditions, active pharmaceutical ingredients (API), or ingredients to add nutritional value or taste.

The solution may be used as such or be mixed to other products.

The solution of the invention could be used for solubilization and stabilization of stilbenoids into water based foods and medical applications. Solutions may further contain one or several pH buffer and other solutes.

In a further aspect, the invention is directed to the use of solutions described herein in the field on medicine and nutrition, particularly parenteral nutrition.

The invention provides with an aqueous solution as described herein for use as a medicament or for use in therapy or surgery.

Particularly, the invention provides with an aqueous solution as described herein for use in peritoneal dialysis, parenteral nutrition and treatment of peritoneal disease or disorders, including but not restricted to complications with peritoneal dialysis, Ascites, Peritonitis, other peritoneal inflammatory disorders such as Familial Mediterranean Fever, and retroperitoneal inflammation, peritoneal infections, primary and secondary benign and malign peritoneal tumors and cancers, or other diseases that may impact the peritoneum, such as superior mesenteric Artery Syndrome, splenic injury and hemoperitoneum, ruptured ectopic pregnancy, peritoneal treatment before, during or after surgery.

The solution may be applied to local or systemic treatments by oral, bucal, nasal, occular, auricular, laringite, stomach, intestinal, hair capillary, finger nail, dermal, below the tongue, genital, rectal, intraperitoneal, intravenal or other subcutaneal application.

The solution may be applied as a food additive with increased stilbenoid content to liquid and/or solid food.

The solution may comprise pH buffering or other additives to further alter stability and/or solubility of stilbenoids.

Manufacturing of the solution:

Solubilization of solubility enhancing saccharides or hydrophilic stilbenoids may be done prior or at the same time than solubilization of hydrophobic stilbenoids. Solubilization of stilbenoids may occur at any temperature allowing solubilization, including during heat/pressure cooking or sterilization, with or without stirring or sonication or other dissolution accelerating techniques.

Following, specific combinations of concentrations of stilbenoid and saccharide are described. In the below embodiments, a preferred stilbenoid is resveratrol or piceid. In a) and b) resveratrol is preferred. In c) and d), piceid is preferred. A preferred monosaccharide is glucose. A preferred oligosaccharide is a polyglucose, particularly a maltodextrin such as icodextrin.

Concentrations of stilbenoid in the present invention are measured after 1 hour stirring at room temperature, which is preferably 20-23° C., more preferably 22°. So, stilbenoid concentrations correspond to measured solubility after 1 hour stirring at room temperature. Concentration is measured in aqueous solution, comprising the stilbenoid and the at least one saccharide. If not specifically indicated, or if not specifically indicated otherwise, the time of stirring is one hour. In some cases, other stirring times are indicated, such as 12 hours. The fact that solubility after one hour stirring cannot be equated with absolute concentration is illustrated by the fact that for example the concentration of resveratrol after 1 hour stirring between 10 and 15 mg/L evolves above 24 mg/L after 12 hours. Further Examples have shown that, specifically at low saccharide concentrations, solubility after 1 hour can significantly vary, with IRT temperature variations of 1 to 2° C., the volume of the test-solution, and stirring speed. Strongest variations were accounted for solubility of Resveratrol in distilled water with values between 1 and 6.5 mg/ml. With increasing concentrations of saccharides, less variations were observed. This is highly beneficial for pharmacological formulations.

a) stilbenoid, preferably resveratrol, and monosaccharide

| monosaccharide | 0.024% by weight until saturation |
|---|---|
| stilbenoid | 6-15 mg/L (1 hour stirring) |
| stilbenoid | 6-30 mg/L (12 hour stirring) | b) stilbenoid, preferably resveratrol, and polysaccharide, preferably Icodextrin,

| polysaccharide | 0.024%-7.5% by weight |
|---|---|
| stilbenoid | 6-120 mg/L | more preferably:

| polysaccharide | 0.75%-7.5% by weight |
|---|---|
| stilbenoid | 15-120 mg/L | c) Stilbenoid and monosaccharide

| monosaccharide | 0.024%-47% by weight |
|---|---|
| stilbenoid | 170-500 mg/L | more preferably:

| monosaccharide | 0.75%-47% by weight |
|---|---|
| stilbenoid | 190-500 mg/L | d) stilbenoid and polysaccharide

| polysaccharide: | 0.024%-7.5% |
|---|---|
| stilbenoid | 270-1600 mg/L | more preferably:

| polysaccharide: | 0.75%-7.5% |
|---|---|
| Stilbenoid | 320-1600 mg/L |

Molecular weight in the present invention is preferably measured by gel permeation chromatography (GPC), preferably gel permeation chromatography with light scattering and refractive index detection (GPC-RI-MALLS). A more detailed, but non-limiting, method is given in the examples. A number of polysaccharide units, which corresponds to a degree of polymerization, can be determined with these methods.

EXAMPLES

Methods

Figure 1:
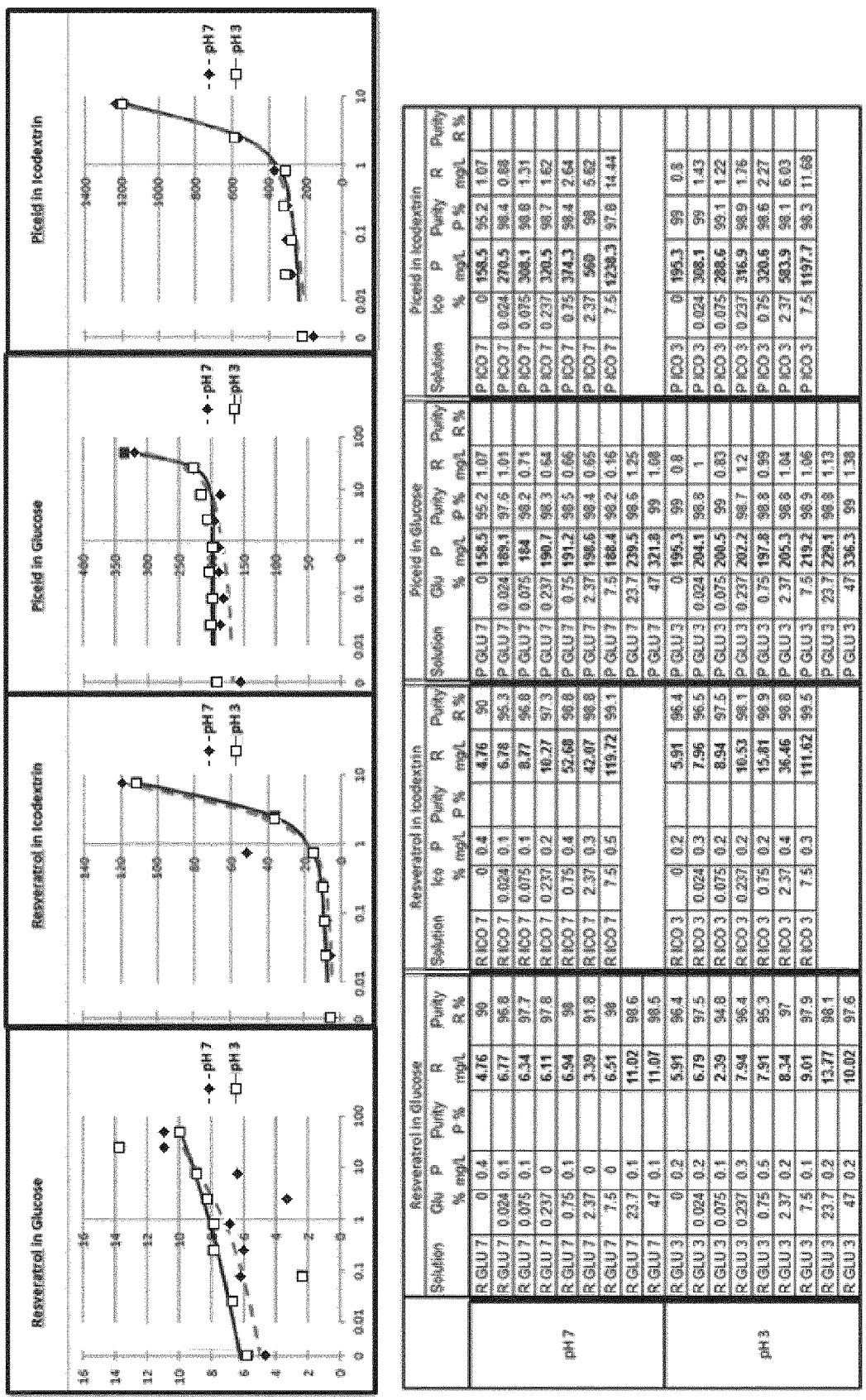
FIG. 1 Solubility and stability of Resveratrol and Piceid after stirring as a function of glucose or icodextrin concentration.

Molecular weight measurement:

The saccharides are dissolved in extra-pure water in a concentration of 0.5% (w/v). The solutions are heated at 95° C. for 30 minutes. The polymers are analyzed using the following devices: Alliance chromatography system (Waters corporation, Milford, Mass., USA), DAWN-EOS light scattering detector (Wyatt Technology, Santa Barbara, USA) with $\lambda 0=658$ nm and 16 detectors in the range of angles from 14.4 to 163.3°, K5 flow cell. The polymers are fractionated on a precolumn and three columns having the separation ranges $300\text{-}10^4$, $5\times10^4\text{-}2\times10^6$ and $10^6\text{-}10^8$ (SUPREMA-Gel, PSS Polymer Standards Service GmbH, Mainz, Germany). 100 µl of solution are injected. The fractionation takes place at a temperature of 30° C. and a flow rate of 0.8 ml/min with 0.05M $NaNO_3$ as eluent. The Astra V 5.1.8.0 program (from Wyatt Technology, Santa Barbara, USA) is used to analyze the molecular weight distribution of the samples. Same procedure can be used when molecular weight of other compounds than saccharides are measured.

Summary and Conclusions from the Examples

At concentrations of less than 0.1% saccharides, particularly glucose and icodextrin, increase stability of stilbenoids by a factor of 2 to 10. Monosacharides such as glucose at concentration above 20% and oligo/poly-saccharides such as icodextrine at concentrations up to 1% increase solubility of stilbenoids within one hour by 2 to 3 times. Oligosaccharides at concentrations of 7.5% and higher increase absolute solubility of stilbenoids by a factor of 3 to 10 and increase solubility within one hour of stilbenoids by a factor of 10 to 20 and higher.

In an approach independent from this patent application, we tested and showed, that certain stilbenoids decrease cytotoxic side-effects of peritoneal therapeutic fluids, thereby increasing biocompatibility of such solutions. When testing stilbenoid solubility in such solutions, we surprisingly found increased solubility and stability of stilbenoids in solutions containing mono- and/or oligo-saccharides. To further characterize this observation we systematically studied impact of mono- and oligo-saccharides on solubility and stability of stilbenoids. We found that monosaccharides and/or oligo-saccharides, particularly glucose and icodextrin, at concentrations as low as 0.0024% (the lowest tested concentration in examples) already significantly stabilize stilbenoids. We further found that concentrations of monosaccharides of 20% and higher further increase solubility, further stabilize stilbenoids, and further increase solubility of resveratrol within one hour, and increase absolute solubility of piceid one and a half to two times. We also found that a mixture of oligo-saccharides at 7.5% increases stability, solubility within one hour, and absolute solubility of stilbenoids. For example, solubility of resveratrol within one hour increases 20 to 25 times and absolute solubility increases at least 3 to 4 times under such conditions. Between 0.0024% and 7.5% of oligo-saccharide concentration, resveratrol stability further increases about ten times. Highest stability of stilbenoids was observed at highest tested concentrations (e.g. 47% mono-saccharide and 7.5% oligo-saccharide). To those skilled in the field, it is to be expected that the phenomenon continues to further increase the concentration above 7.5% (highest tested concentration of oligo-saccharides) of oligo-saccharides, and that lower concentrations that 0.0024% (our lowest tested concentration of saccharides) may still have measurable effects.

The here described general impact of mono- and oligo-saccharides on solubility of stilbenoids has been tested in commercially available peritoneal dialysis solutions:

Fresenius Safestay® 1.5% glucose, Baxter Physioneal® 3.86% glucose and Baxter Extraneal® (7.5% icodextrin), precisely in acid glucose solutions, such as applied in two compartment peritoneal dialysis applications Stay Safe® and Physioneal®, as well as in Extraneal® Solution that had previously been acidified to pH3. In all cases we confirmed increased solubility within 1 hour and increased stability of stilbenoids, and an increase of absolute solubility of at least three times for resveratrol in extraneal. Stilbenoids remained stable during a 12 hour stirring experiment at room temperature. Furthermore we tested stability of stilbenoids in these solutions, after submission to heat sterilization.

It appears to us that we have uncovered a widely applicable method for solubilizing and stabilizing stilbenoids in aqueous solutions that might be used for many nutritional, medical, and/or general health applications. It appears that there is a relation between the molecular weight of a saccharide and the effect on stilbenoid solubility and stability.

In certain cases, solubilization of a stilbenoid takes one to several hours or even longer. This may be the reason why the here discovered phenomenon has not been described before.

It is important to understand that increased solubility and stability within 1 hour stirring is also of high importance for application of resveratrol at much lower concentrations than those here obtained. Indeed, an absolute concentration of 30 mg/L does not help if the stilbenoid falls out due to temperature variations worth, if spontaneously re-solubilization at room temperature, or application temperature, does not occur. For example biological activity of resveratrol has been described in between concentrations 0.5 μm and several mM, corresponding to weights between 0.1 mg/L and several g/L. Even at concentrations as low as 0.1 mg/L, a robust solubility and stability of the stilbenoid should be guaranteed in aqueous solutions, which has not been the case previously. Adaptation of pH to at least pH 3 and/or addition of at least 0.02% saccharides allows stable dissolution and stability of such quantities of resveratrol. Addition of about 5% or more of an oligo-saccharide of an average molecular weight (weight average) between 2 KD and 50 KD allows heat-sterilization of such solution without degradation of the stilbenoid.

SPECIFIC EXAMPLES

Purity of tested stilbenoids were
for resveratrol between 99.86% and 99.88%
for piceid between 98.89% and 99.12%.
Major impurity in piceid was resveratrol of approximately 1%.

For analysis R and P and their impurities were separated by a C-18 column with a gradient system and UV-detection at 306 nm.

Increase of stability or solubility of a stilbenoid by presence of a saccharide, could only be measured within the range of solubility of the saccharide it self.

Solubility measurements after 1 hour stirring at RT generated some variability in-between measurement series, which might be due to low temperature variations, background measurements and experimental imprecisions. Specifically, variations of concentration of Resveratrol in $H_2O$, without any saccharid, between 0.3 and 6 mg/L were observed in-between different series. As a rule of thumb, for calculating factors of increased solubility, the minimal concentration value of Resveratrol in $H_2O$ was always accounted for at 1.2 mg/L. If, in a given series, Resveratrol concentration in $H_2O$ was higher than 1.2, this higher value was applied to calculate factors of increase of concentration. The here calculated factors of increase of solubility are therefore to be considered as conservative.

Example 1

Solubility and stability of Resveratrol and Piceid after one hour stirring at RT, as a function of glucose or icodextrin concentration in a solution, containing 5.4 g/L NaCl, 4.5 g/L NaLactate, 0.275 g/L CaCl2, and 0.051 g/L MgCl2, buffered at pH 3 or pH 7. Solubility was measured after one hour stirring at room temperature, in presence of excess solute, followed by filtering.

At 0% glucose or icodextrin, pH3 versus Ph7 stabilizes Resveratrol by 2 to 3 times and stabilizes Piceid 3 to 4 times and slightly increases solubility of both stilbenoids.

At pH7, 0.024% of glucose or Icodextrin stabilize tested stilbenoids 2 to 3 times. 0.075% of Glucose or Icodextrin stabilize tested stilbenoids 3 to 4 times.

High concentrations of Glucose (24 and 47%), but concentration of Icodextrin of only 0.075%, completely stabilize the tested stilbenoids within the limits of detection and increase their solubility within one hour by a factor 1.5 to 2.

Highest tested glucose concentrations increased solubility after 1 hour of resveratrol by a factor of 2 to 3, and of piceid by 1.5 to 2.

Concentration of 2.4% Icodextrin increase solubility within one hour of resveratrol 7 to 10 times, and of piceid 3 to 4 times. Concentration of Icodextrin of 7.5% increase solubility within one hour of resveratrol by a factor of 20 and absolute solubility at least 3.5 times. It increases solubility after one hour of piceid by a factor of 6 to 8. In case of piceid, measured solubility within one hour equals absolute solubility, since total solubilization happens within the first five minutes.

The results of Example 1 are shown in FIG. 1. FIG. 1 shows the data in four charts and four tables that are related to the charts, repectively.

Example 2

Stability of resveratrol and piceid in commercially available (in one case pH adjusted) dialysis solutions.

Solubility studies were carried out commercially available peritoneal dialysis solutions Fresenius Safestay® 1.5% glucose, Baxter Physioneal® 3.86% glucose and Baxter Extraneal® (7.5% icodextrin), precisely in acidic glucose solutions, such as applied in two compartment peritoneal dialysis applications Stay Safe® and Physioneal®, as well as in Extraneal® Solution that had previously been acidified to pH3. Medium B (117.14 g/L glucose monohydrate (equivalent to 106.5 g/L anhydrous glucose), 0.507 g/L Calcium chloride dihydrate, 0.140 g/L Magnesium chloride hexahydrate, measured pH 3.5), Medium E (75 g/L Icodextrin, 5.35 g/L Sodium Chloride, 4.48 g/L Sodium Lactate, 257 mg/L Calcium Chloride USP, 50.8 mg/L Magnesium Chloride USP, adjusted to pH 3 in our lab), and Medium F (30 g/L anhydrous glucose, 11.279 g/L Sodium chloride, 0.3675 g/L Calcium chloride dihydrate, 0.2033 g/L Magnesium chloride hexahydrate, measured pH 3).

Solubility was measured after 5 minutes to 12 hours stirring at room temperature, in presence of excess solute, followed by filtering.

Figure 2:
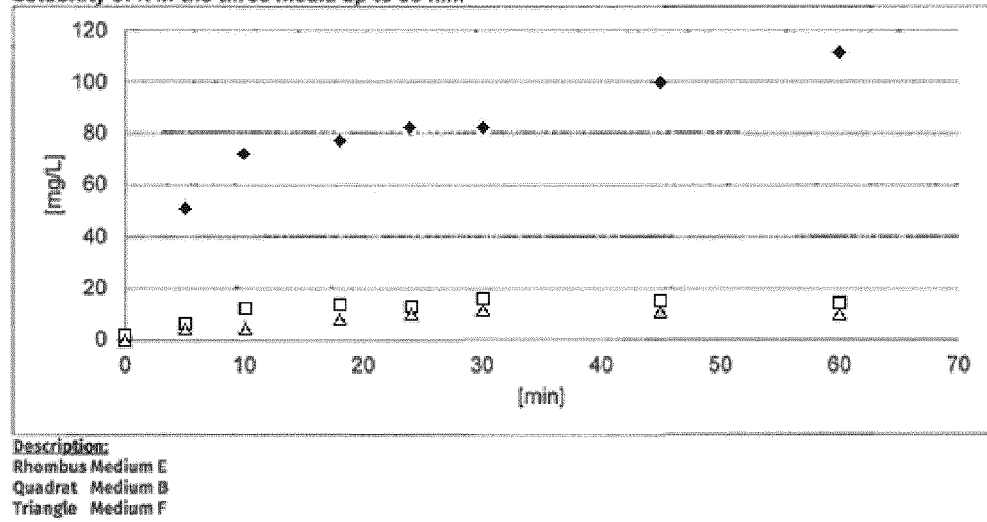
FIG. 2 Stability of resveratrol and piceid in commercially available (in one case pH adjusted) dialysis solutions.

FIG. 2 shows the resulting data as a chart and in a related table.

Solubilization saturation curves measured in commercial dialysis solutions confirmed the applicability of increased stability and solubility by saccharides. Solubilities obtained for resveratrol after 12 hours in glucose approached referred absolute solubility of Resveratrol in aqueous solution (approximately 30 mg/L). Solubility of resveratrol in 7.5% Icodextrin depassed that value about 4 times.

Results for analyte P:

| Test solution after Stirring-Time [min] | P in Medium B found [mg/L] | P in Medium E found [mg/L] | P in Medium F found [mg/L] |
| --- | --- | --- | --- |
| 60 | 485.6 | 1585.5 | 493.8 |
| 12 h | 342.9 | 1370.3 | 461.4 |

Solubilization of piceid took place within the first minutes and was stable between 1 and 12 hours. Again the results obtained in commercial dialysis solutions are well in range of expectations from established solubility curves in 5.4 g/L NaCl, 4.5 g/L NaLactate, 0.275 g/L CaCl2, and 0.051 g/L MgCl2.

Solubility was measured after one hour or 12 hours stirring at room temperature, in presence of excess solute, followed by filtering.

Example 3

Stability of stilbenoids in commercial dialysis solutions after 1 hour and 12 hours stiring at room temperature:

Stability was measured after one hour or 12 hours stirring at room temperature, in presence of excess solute, followed by filtering.

Purity of the 60 Min Values

| Name | P Area % | P cis Area % | R Area % | R cis Area % |
| --- | --- | --- | --- | --- |
| R B | — | — | 100 | — |
| R E | 0.10 | — | 99.90 | — |
| R F | — | — | 100 | — |
| P B | 98.83 | 0.04 | 0.89 | 0.06 |
| P E | 98.87 | 0.01 | 0.98 | 0.03 |
| P F | 98.87 | 0.03 | 0.86 | 0.07 |

Purity of the 12 h Values

| Name | P Area % | P cis Area % | R Area % | R cis Area % |
| --- | --- | --- | --- | --- |
| R B | 0.54 | — | 98.19 | 0.65 |
| R E | 0.14 | — | 99.48 | 0.21 |
| R F | 0.44 | — | 99.00 | 0.25 |
| P B | 97.80 | 0.18 | 1.69 | 0.10 |
| P E | 98.52 | 0.06 | 1.24 | 0.03 |
| P F | 98.15 | 0.14 | 1.41 | 0.09 |

Within the limits of detection, the tested stilbenoids appeared stable in 3 commercial dialysis solutions.

Example 4

Stability of Resveratrol in commercial dialysis solutions during autoclavation. Experiment was carried out in previous defined media B, E and F. 25 mg of resveratrol were sonicated in each medium and 0.45 μm filtered to give clear solutions. Obtained solutions were autoclaved for 30 min at 121° C.

Purity after Autoclaving

| Name | P Area % | P cis Area % | R Area % | R cis Area % |
| --- | --- | --- | --- | --- |
| R B | 1.10 | 0.22 | 94.54 | 1.45 |
| R E | 0.04 | — | 99.17 | 0.33 |
| R F | 0.56 | — | 97.40 | 0.70 |

Resveratrol stability in saccharide containing dialysis solutions at pH3, during standard heat-sterilization, was remarkably high, specifically in presence of 7.5% Icodextrin.

Example 5

Figure 3:
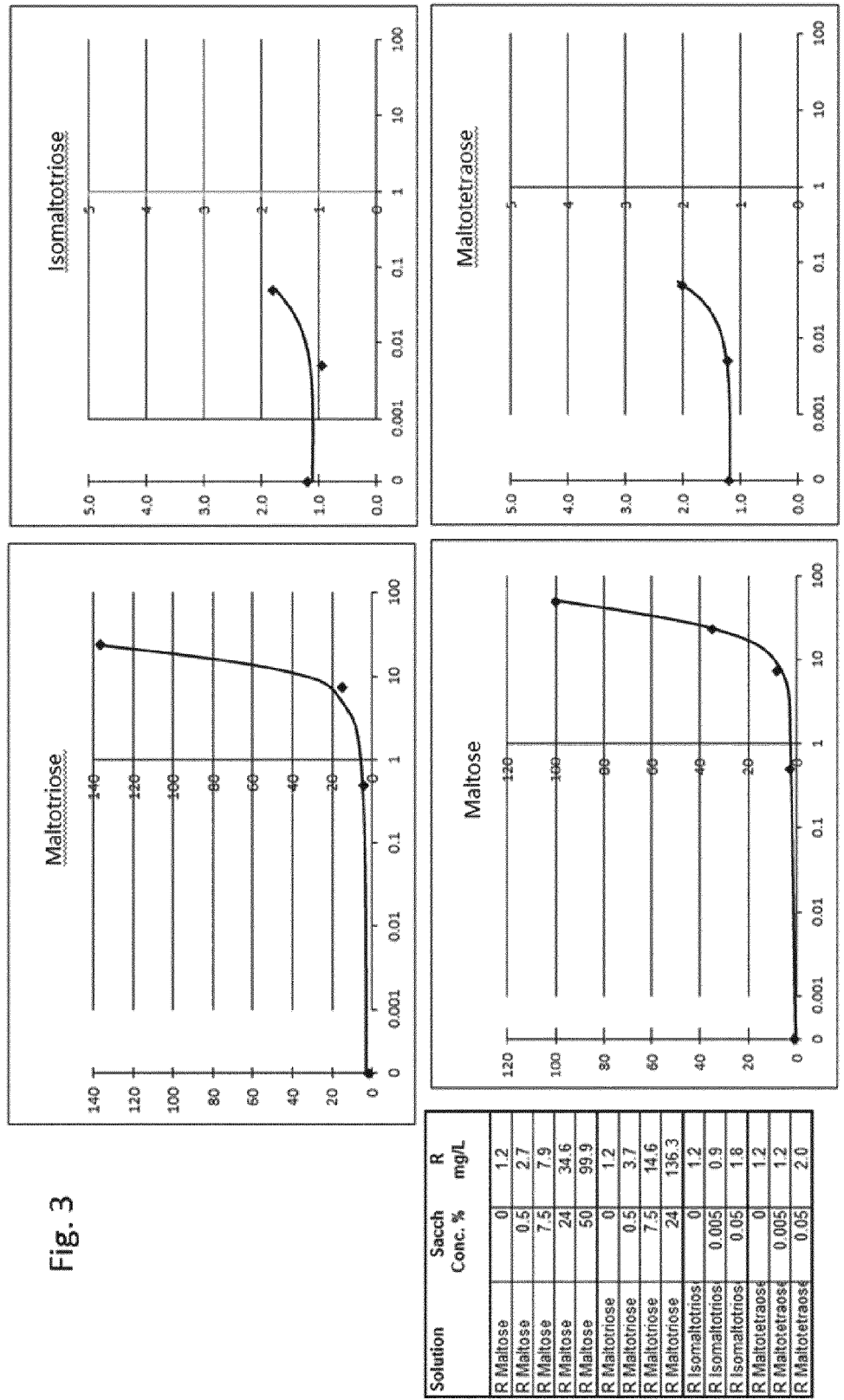
FIG. 3 Solubility of Resveratrol after one hour stirring at RT, as a function of the concentration of Maltose, Maltotriose, Isomaltotriose, and Maltotetraose.

Solubility of Resveratrol after one hour stirring at RT, as a function of the concentration of Maltose, Maltotriose, Isomaltotriose, and Maltotetraose in $H_2O$. Solubility was measured after one hour stirring at room temperature, in presence of excess solute, followed by filtering. The results of Example 5 are shown in FIG. 3, which shows the data in four charts and four tables that are related to the charts, respectively. Concentrations of 0.05% of Isomaltotriose and Maltotetraose increased solubility of the stilbenoid resveratrol by a factor of 1.5 and 1.8 respectively. Concentration of 0.5% maltose and maltotriose, increased stilbenoid solubility by a factor of 2.2 and 2.6 respectively. Concentration of Maltose and maltotriose of 7.5% increased solubility of the stilbenoid resveratrol by a factor higher than 6 and 3 respectively. Concentrations of Maltose and maltotriose of 24% increased solubility of the stilbenoid resveratrol by a factor of 29 and 4 respectively; Concentration of maltose of 50% increased solubility of the stilbenoid resveratrol by a factor of 100.

Example 6

Figure 4:
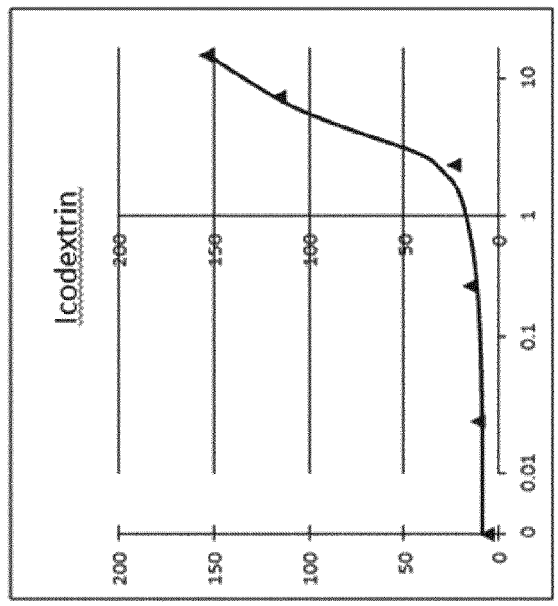
FIG. 4 Solubility of Resveratrol after one hour stirring at RT, as a function of the concentration of Maltodextrin DE 16-19 (DE=dextrose equivalents), Maltodextrin DE 4-7 or Icodextrin.
Figure 4:
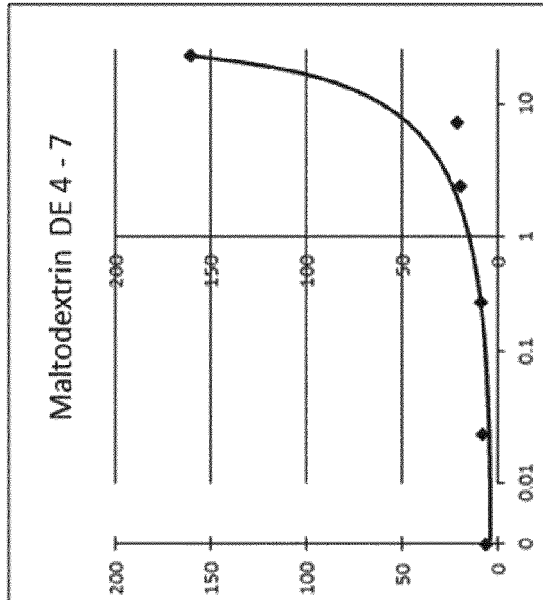
Figure 4:
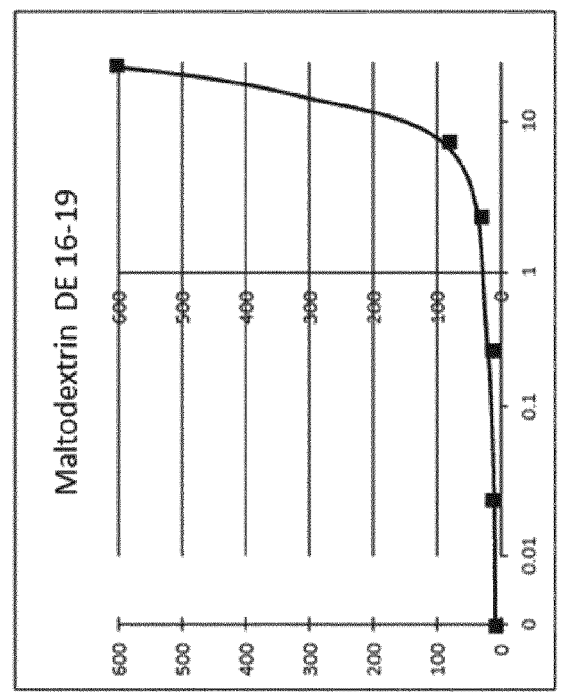

Solubility of Resveratrol after one hour stirring at RT, as a function of the concentration of Maltodextrin DE 16-19 (DE=dextrose equivalents), Maltodextrin DE 4-7 or Icodextrin in $H_2O$. Solubility was measured after one hour stirring at room temperature, in presence of excess solute, followed by filtering. The results of Example 6 are shown in FIG. 4, which shows the data in three charts and three tables that are related to the charts, respectively. Concentration of Maltodextrin DE16-19, Maltodextrin DE4-7 and Icodextrin of 0.24% increase solubility of the stilbenoid resveratrol by a factor of 1.5 to 3. Concentration of Maltodextrin DE16-19, Maltodextrin DE4-7 and Icodextrin of 2.4% increased solubility of stilbenoid by 3.3 to 4.7 times. Concentration of Maltodextrin DE16-19, Maltodextrin DE4-7 and Icodextrin of 7.5% increased solubility of the stilbenoid resveratrol by a factor of 13, 3.5 and 19, respectively. Concentration of 15% Icodextrin increased solubility of the stilbenoid resveratrol by a factor of 26. Concentration of 24% of Maltodextrin DE16-19, Maltodextrin DE4-7, increase solubility of the stilbenoid resveratrol by a factor of 100 and 27 respectively.

Example 7

Figure 5:
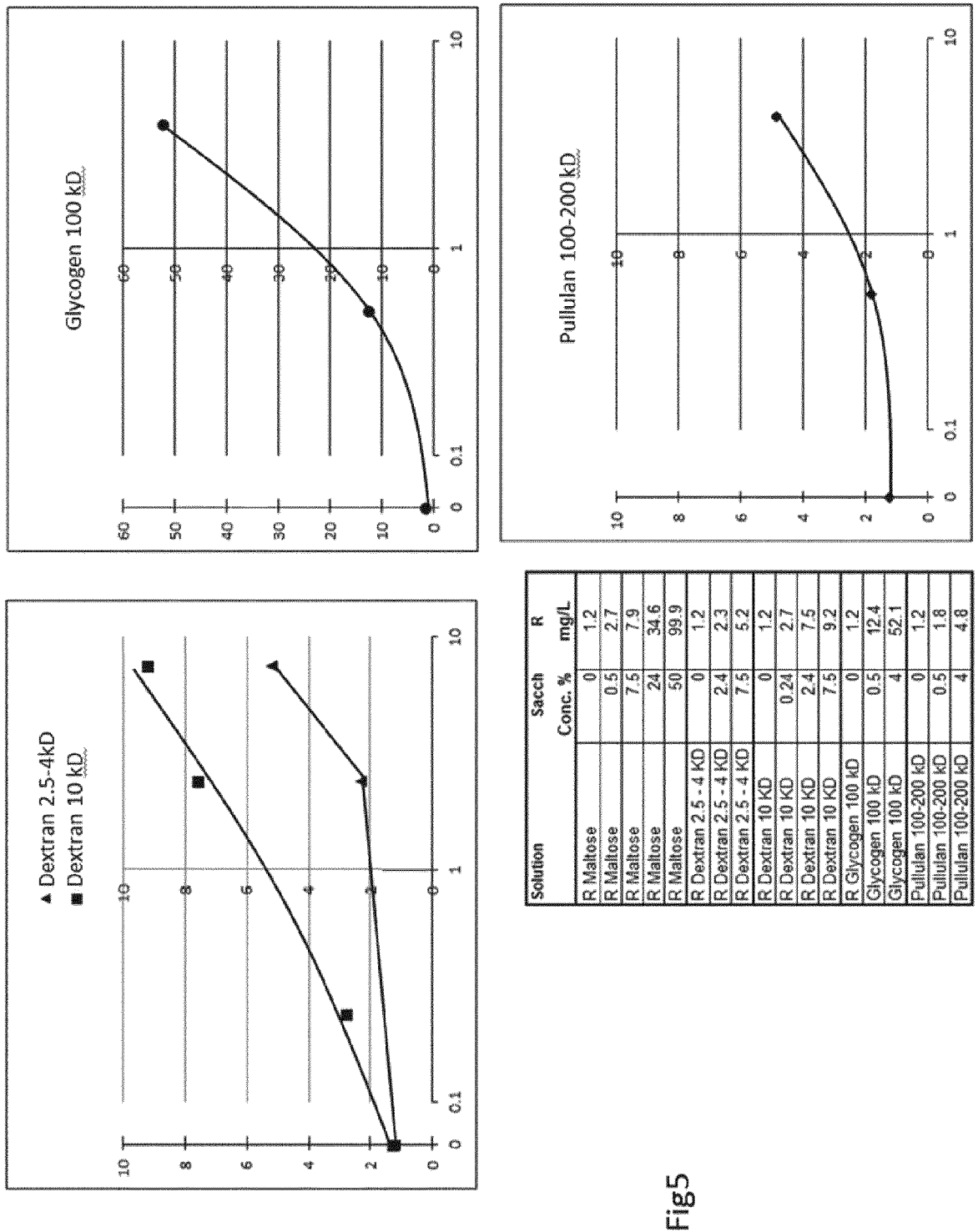
FIG. 5 Solubility of Resveratrol after one hour stirring at RT, as a function of the concentration of Dextran 2.5-4 kD, Dextran 10 kD, Glycogen 100 kD, and Pullulan 100-200 kD.

Solubility of Resveratrol after one hour stirring at RT, as a function of the concentration of Dextran 2.5-4 kD, Dextran 10 kD, Glycogen 100 kD, and Pullulan 100-200 kD, in $H_2O$. Solubility was measured after one hour stirring at room temperature, in presence of excess solute, followed by filtering. The results of Example 7 are shown in FIG. 5, which shows the data in four charts and four tables that are related to the charts, respectively. Concentration of 0.24% Dextran 10 kD increased solubility of the stilbenoid resveratrol by a factor of 2.3. Concentrations of 0.5% of Glycogen 100 kD and Pullulan 100 to 200 kD increased solubility of the stilbenoid resveratrol by a factor of 10 and 1.5 respectively. Concentration of 2.4% Dextran 10 kD increased solubility of the stilbenoid resveratrol 6.3 times. Concentration of 4% Glycogen 100 kD and Pullulan 100 to 200 kD increased solubility of the stilbenoid resveratrol by a factor of 43 and 4 respectively. Concentration of 7.5% Dextran 2.5-4 kD and dextran 10 kD increased solubility of the stilbenoid resveratrol by a factor of 2.7 and 7.7 respectively.

Example 8

Figure 6:
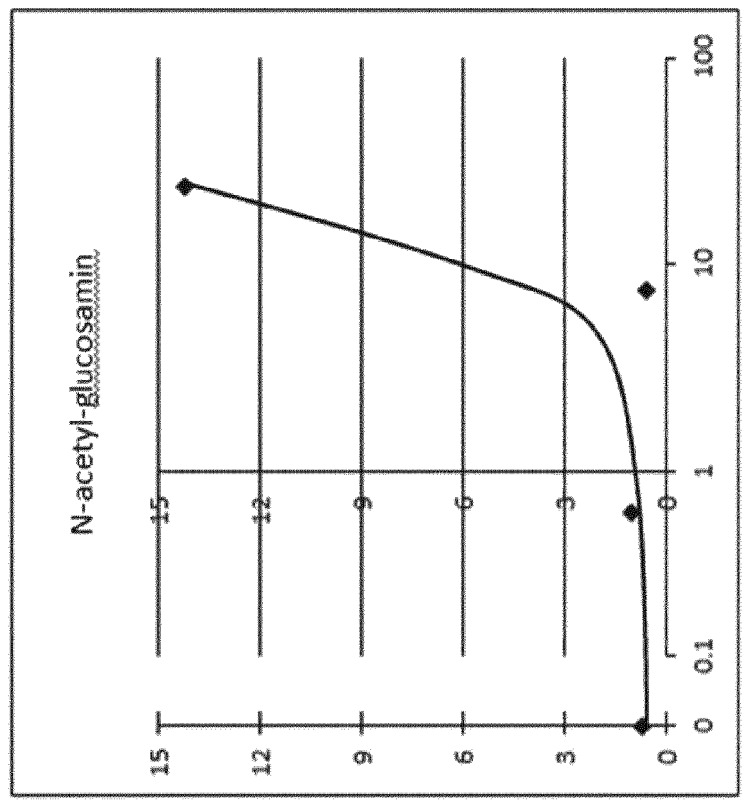
FIG. 6 Solubility of Resveratrol after one hour stirring at RT, as a function of the concentration of N-acetyl-glucosamine.

Solubility of Resveratrol after one hour stirring at RT, as a function of the concentration of N-acetyl-glucosamin in H2O. Solubility was measured after one hour stirring at room temperature, in presence of excess solute, followed by filtering. The results of Example 8 are shown in FIG. 6, which shows the data in a chart and a related table. Concentration of 24% of N-acetylglucosamin increased concentration of the stilbenoid resveratrol 12 times.

Example 9

Figure 7:
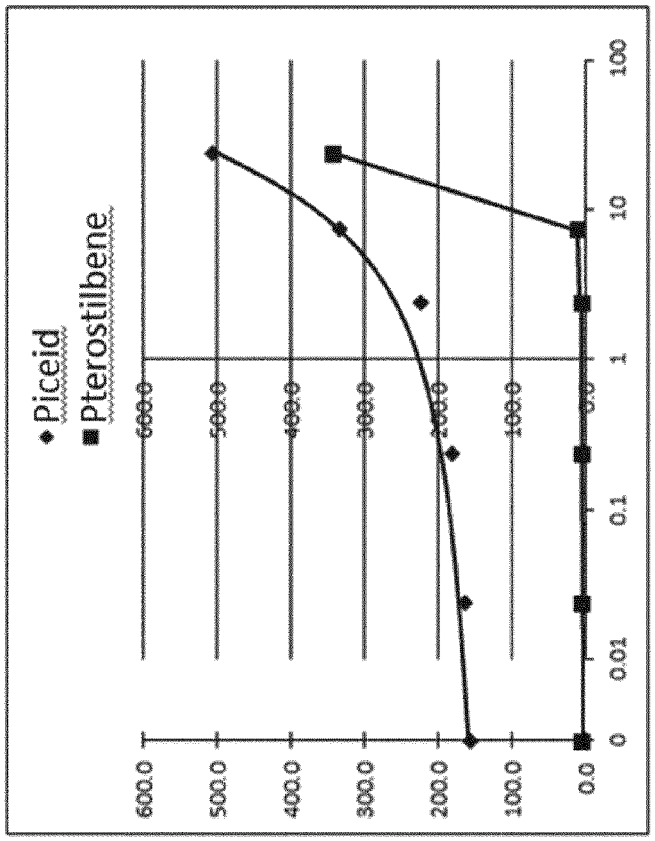
FIG. 7 Solubility of Piceid (Polydatin) and Pterostilbene as functions of the concentration of Maltodextrin DE 16-19.

Solubility of Piceid (Polydatin) and Pterostilbene as functions of the concentration of Maltodextrin DE 16-19 in H2O. Solubility was measured after one hour stirring at room temperature, in presence of excess solute, followed by filtering. The results of Example 9 are shown in FIG. 7, which shows the data in two charts and two tables that are related to the charts, repectively. Concentration of 2.4% Maltodextrin DE16-19 increased solubility of Piceid by a factor of 1.4. Concentration of 7.5% increased solubility of Piceid and Pterostilbene by a factor of 2.1 and 13 respectively. Concentration of 24% Maltodextrin D16-19 increased solubility of stilbenoid Piceid and pterostilbene by a factor of 3.2 and 100 respectively.

Example 10

Figure 8:
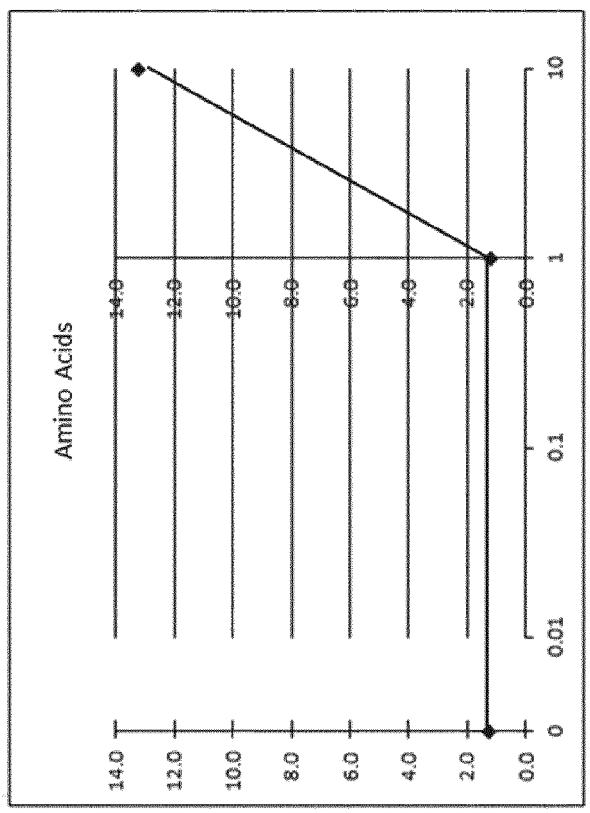
FIG. 8 Solubility of Resveratrol in different amino acid containing solutions.

Solubility of Resveratrol in different amino acid containing solutions, compared to $H_2O$. Solubility was measured after one hour stirring at room temperature, in presence of excess solute, followed by filtering. The results of Example 10 are shown in FIG. 8, which shows the data in a chart and a related table. Two medical preparations of Amino acid solution were tested and compared against water for solubility of stilbenoid Resveratrol. An increased solubility of stilbenoid Resveratrol by a factor of 11 was observed in Aminoven®, containing 10% of amino acids.

What is claimed is:

1. A method for increasing the solubility of a stilbenoid in water, comprising:
    dissolving a saccharide which is selected from the group consisting of a monosaccharide, a disaccharide and a trisaccharide, or a mixture of distinct saccharides thereof, in a predetermined concentration of ≥0.75% by weight (7.5 g/L) in a water-containing solution, and
    dissolving the stilbenoid in the water-containing solution that contains the dissolved saccharide to form an aqueous solution, wherein at least two times increase in solubility of the stilbenoid is detected in the presence of the predetermined concentration of the saccharide;
    wherein the stilbenoid is selected from the group consisting of resveratrol, a resveratrol derivative, piceatannol, pterostilbene and dihydro-resveratrol;
    wherein the resveratrol derivative is selected from one of piceid and the following compounds 1-9, 11, 12, 15, 16, 17 and 18:

(1) 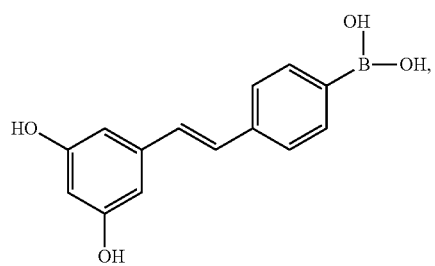
(2) 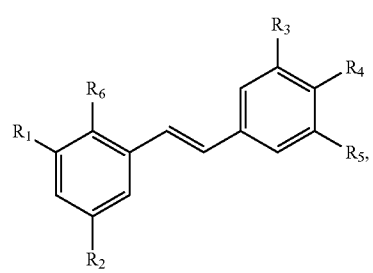
(3) 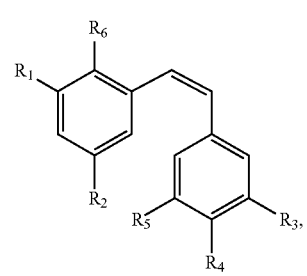
(4) 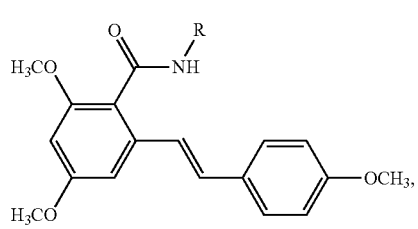
(5) 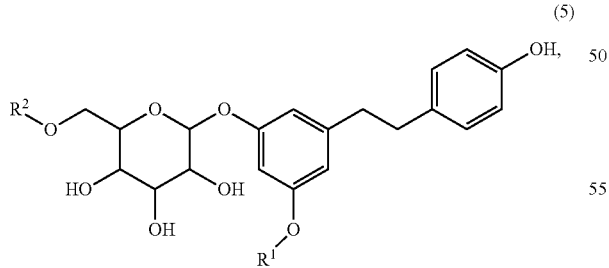
(6) 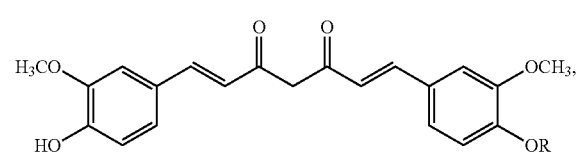
(7) 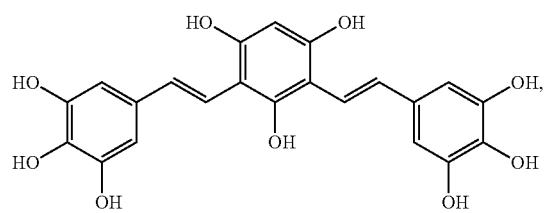
(8) 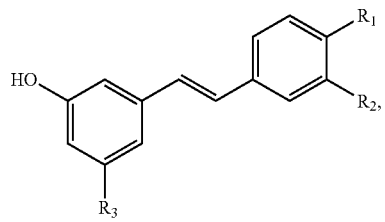
(9) 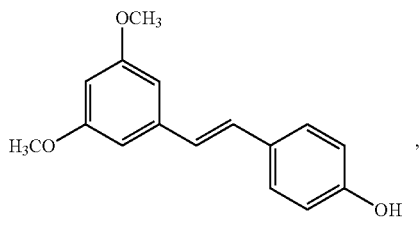
(11) 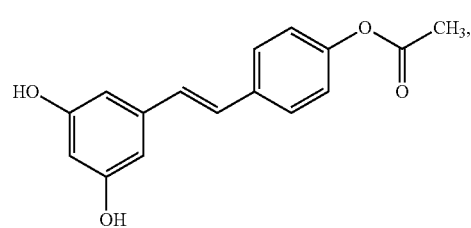
(12) 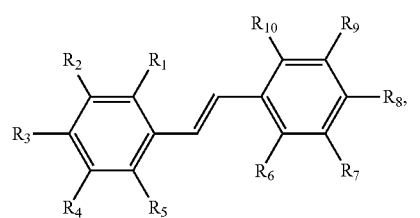
(15) 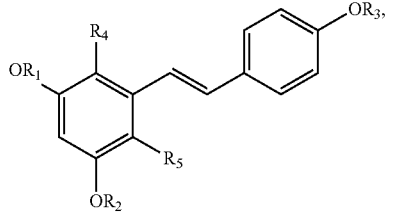
(16) 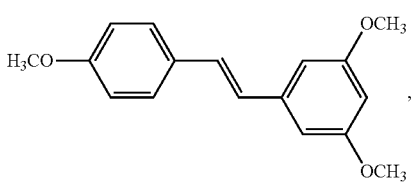

-continued

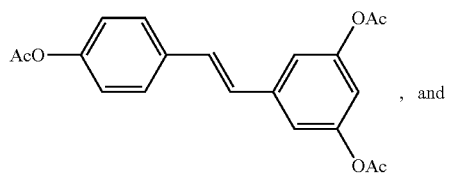

, and

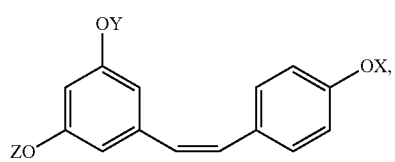

wherein in compound 2 and compound 3,
$R_1=R_2=R_4=OCH_3$, $R_3=R_5=R_6=H$; or
$R_1=R_2=R_4=OCH_3$, $R_3=R_5=H$; $R_6=OH$; or
$R_1=R_2=R_3=R_5=OCH_3$, $R_4=H$; $R_6=H$; or
$R_1=R_2=R_3=R_5=OCH_3$, $R_4=H$; $R_6=OH$; or
$R_1=R_2=R_3=R_4=OCH_3$, $R_5=H$; $R_6=H$; or
$R_1=R_2=R_3=R_4=OCH_3$, $R_5=H$; $R_6=OH$ wherein in compound 4, R is one of the following moieties:

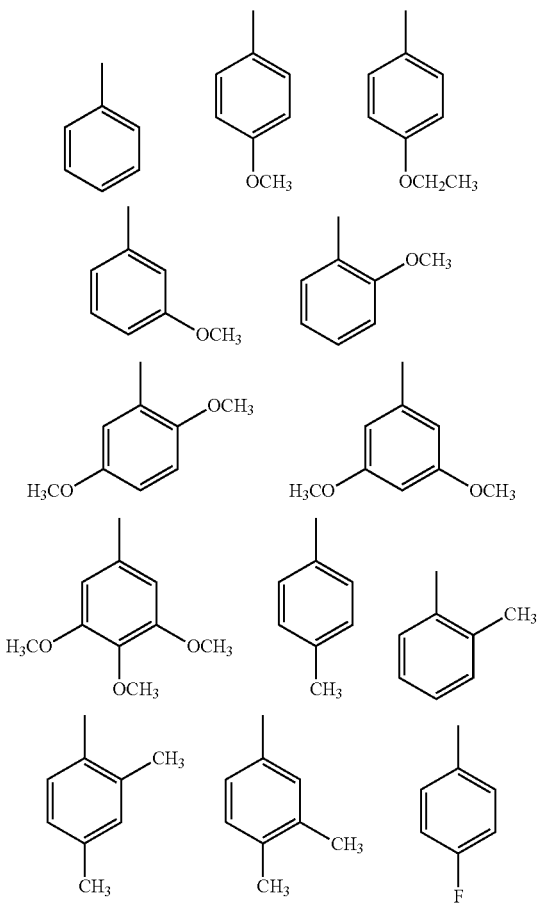

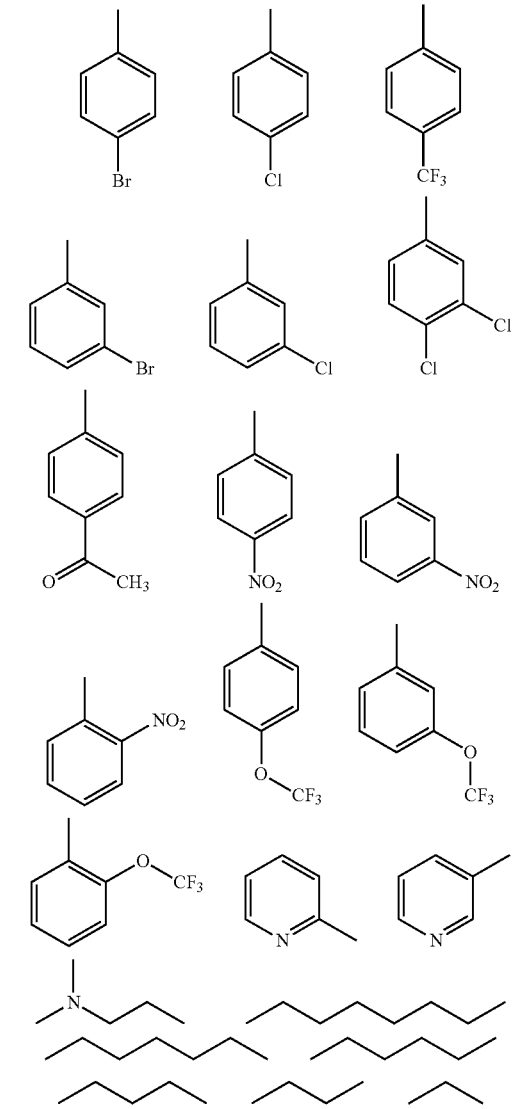

wherein in compound 5, $R_1$ is hydrogen or a group of formula

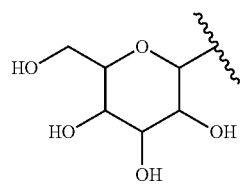 [SMILES: *C1OC(CO)C(O)C(O)C1O]

$R_2$ is hydrogen or forms together with the oxygen to which it is bound an acyl group (—OCO—$R_3$), wherein $R_3$ is a C1-C22 alkyl group or a C2-C22 alkenyl group, wherein, if $R_2$ is hydrogen $R_1$ is the formula defined in compound 5 above, wherein in compound 6, R is one of the following moieties:

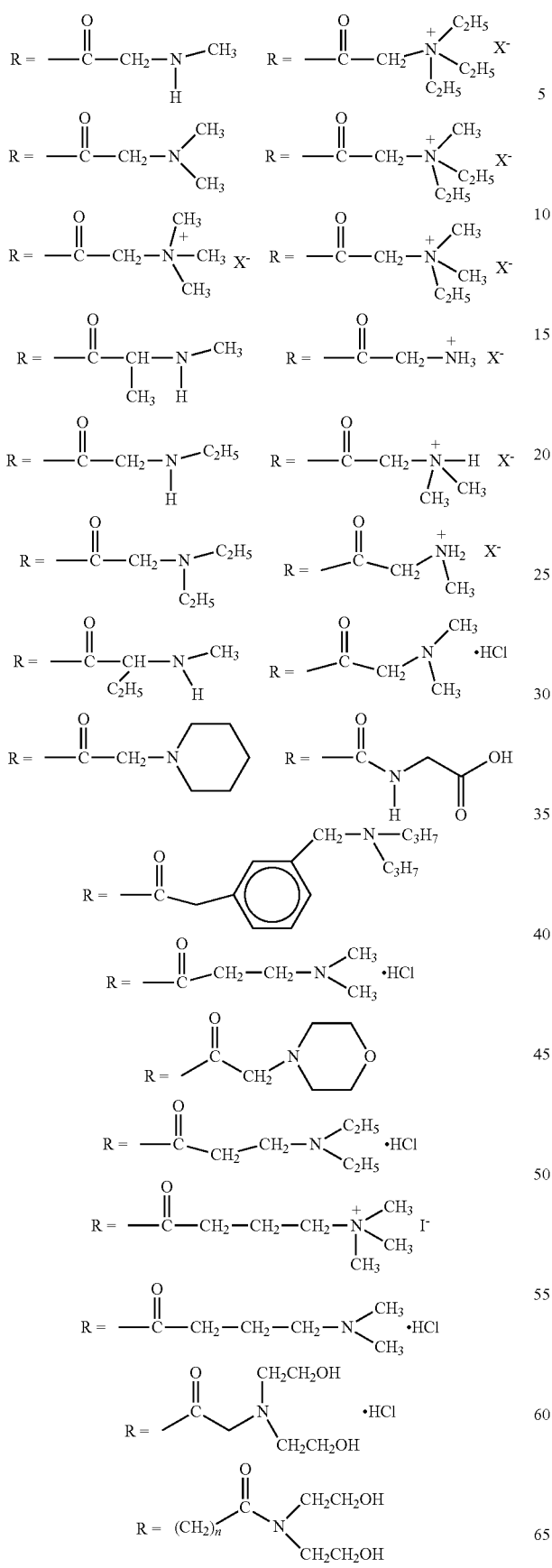
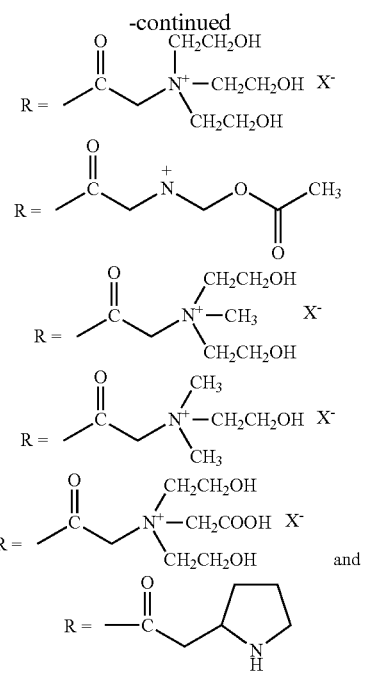
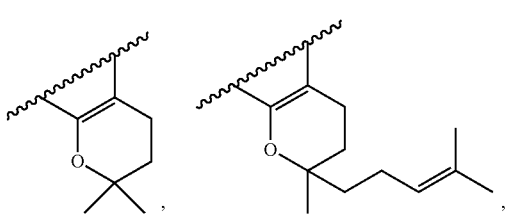

wherein $X^-$ is anion pair of the corresponding cation;
wherein in compound 8,
$R_1$=OCH$_3$, $R_2$=OH, $R_3$=O-Glucose; or
$R_1$=OCH$_3$, $R_2$=H, $R_3$=O-Glucose; or
$R_1$=OCH$_3$, $R_2$=OH, $R_3$=OH; or
$R_1$=OCH$_3$, $R_2$=H, $R_3$=OH; or
$R_1$=OH, $R_2$=OH, $R_3$=O-Glucose; or
$R_1$=OH, $R_2$=OH, $R_3$=OH;
wherein in compound 12,
$R_1$, $R_2$, $R_3$, $R_4$, $R_5$, $R_6$, $R_7$, $R_8$ $R_9$, and $R_{10}$ are independently chosen from hydrogen, hydroxyl, hydrocarbyl, substituted hydrocarbyl, hydrocarbyloxy, substituted hydrocarbyloxy, and sulfoxy;
provided that at least one of the R groups is a hydroxyl or substituted hydroxyl group; and
provided that if compound 12 is monomeric, then compound 12 is other than resveratrol, wherein in compound 15,
$R_1$, $R_2$ and $R_3$, independently from one another, represent H or (C1-C3)alkyl; $R_4$ and $R_5$ are identical or different and are each hydrogen, linear or branched (C1-C5) alkyl, a prenyl group CH$_2$—CH═C(CH$_3$)$_2$, or a geranyl group CH$_2$—CH═C(CH$_3$)(CH$_2$)$_2$CH═C(CH$_3$)$_2$,
or $R_4$ and $R_1$, and independently $R_5$ and $R_2$, together with the atoms they are linked to, form one of the following groups:

with the provisos that $R_4$ and $R_5$ are not both hydrogen and that when $R_1$=$R_2$=$R_3$=H, $R_4$ and $R_5$ are not a prenyl group and hydrogen, respectively, wherein in compound 18, X, Y, and Z are either hydrogen or a protective group, provided that at least one of X, Y, and Z is the protective group.

2. The method according to claim 1, wherein the saccharide is a monosaccharide.

3. The method according to claim 1, wherein the saccharide is a disaccharide.

4. The method according to claim 1, wherein the saccharide is a trisaccharide.

5. The method according to claim 2, wherein the aqueous solution has an acidic pH between 1 and 6.

6. The method according to claim 1, wherein the aqueous solution has an acidic pH between 1 and 6.

7. The method according to claim 1, wherein the aqueous solution has an acidic pH between 1 and 3.5.

8. The method according to claim 1, wherein the aqueous solution has an acidic pH between 1 and 3.0.

9. The method according to claim 1, wherein the concentration of stilbenoid is ≥0.15 mg/L.

10. The method according to claim 1, wherein the saccharide is selected from the group consisting of glucose, fructose, sucrose and maltose, or a mixture of two or more distinct saccharides thereof.

11. The method according to claim 1, wherein the stilbenoid is present in a concentration of 0.1 mg/L to 100 mg/L.

12. The method according to claim 1, wherein the at least one stilbenoid is present in a concentration of 0.02 μM to 315 μM.

13. The method of claim 11, wherein the saccharide is a monosaccharide.

14. The method of claim 11, wherein the saccharide is a disaccharide.

15. A method for increasing the solubility of a stilbenoid, which is selected from the group consisting of resveratrol, a resveratrol derivative, piceatannol, pterostilbene and dihydro-resveratrol, in water, the method consisting of the steps of:

dissolving a saccharide which is selected from the group consisting of a monosaccharide, a disaccharide, a trisaccharide, a reducing alpha-glucan, and a hydrolysis product of an alpha-glucan, or a mixture of distinct saccharides thereof, in a total concentration of ≥0.75% by weight (7.5 g/L) in a water-containing solution, wherein the reducing alpha-glucan has a molecular weight between 350 D and 50 kD, and dissolving the stilbenoid in the water-containing solution that contains the dissolved saccharide to form an aqueous solution, wherein the concentration of the stilbenoid is 0.01 mg/L to 500 mg/L, wherein the resveratrol derivative is selected from one of piceid and the following compounds 1-9, 11, 12, 15, 16, 17 and 18:

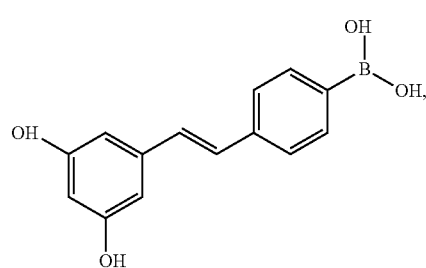

(1)

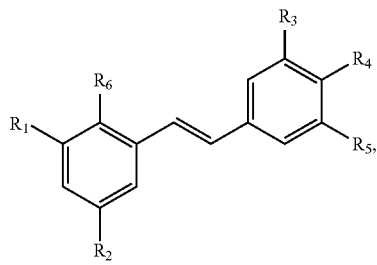

(2)

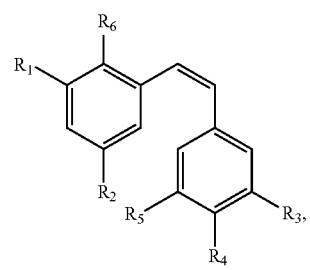

(3)

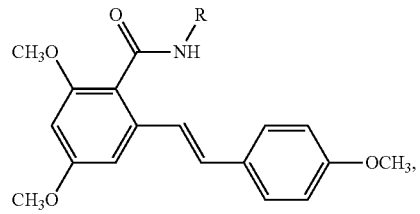

(4)

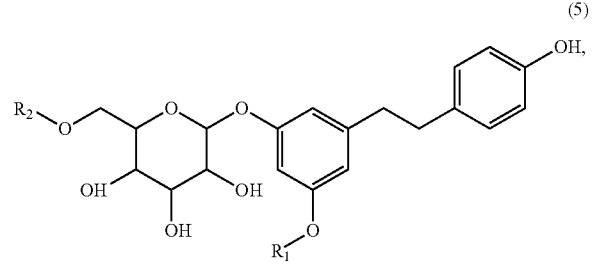

(5)

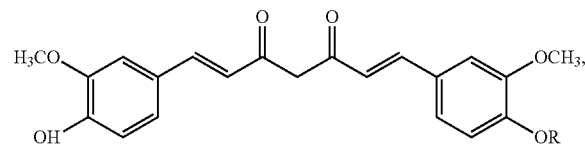

(6)

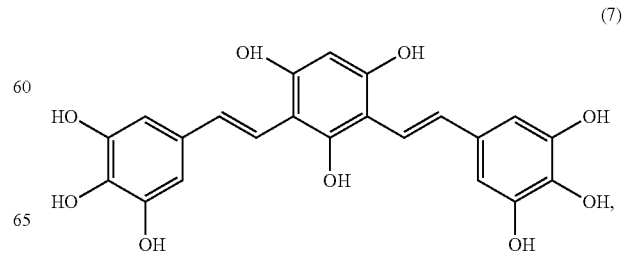

(7)

wherein in compound 2 and compound 3,
R₁=R₂=R₄=OCH₃, R₃=R₅=R₆=H; or
R₁=R₂=R₄=OCH₃, R₃=R₅=H; R₆=OH; or
R₁=R₂=R₃=R₅=OCH₃, R₄=R₆=H; or
R₁=R₂=R₃=R₅=OCH₃, R₄=H, R₆=OH; or
R₁=R₂=R₃=R₄=OCH₃, R₅=R₆=H; or
R₁=R₂=R₃=R₄=OCH₃, R₅=H, R₆=OH; or
wherein in compound 4, R is one of the following moieties:

-continued
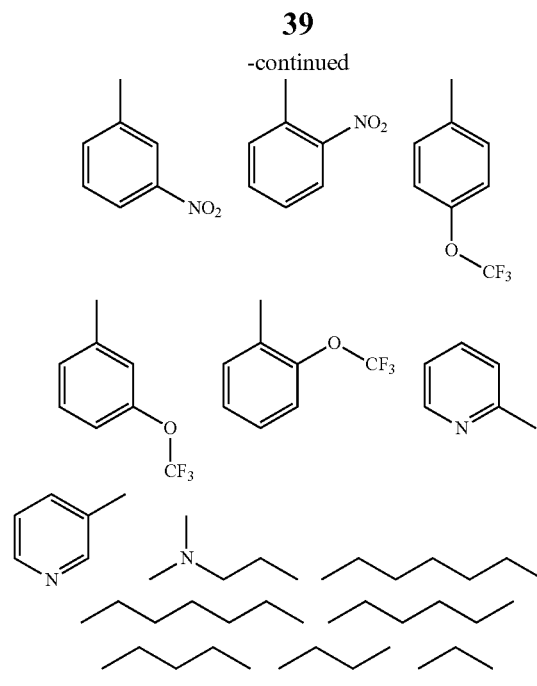
wherein in compound 5,
R₁ is hydrogen or a group of formula
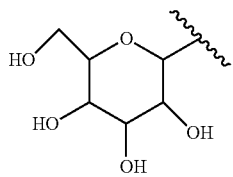 [SMILES: *C1OC(CO)C(O)C(O)C1O]
R₂ is hydrogen or forms together with the oxygen to which it is bound an acyl group (—OCO—R₃),
wherein R₃ is a C1-C22 alkyl group or a C2-C22 alkenyl group,
wherein, if R₂ is hydrogen R₁ is the formula defined in compound 5 above,
wherein in compound 6, R is one of the following moieties:
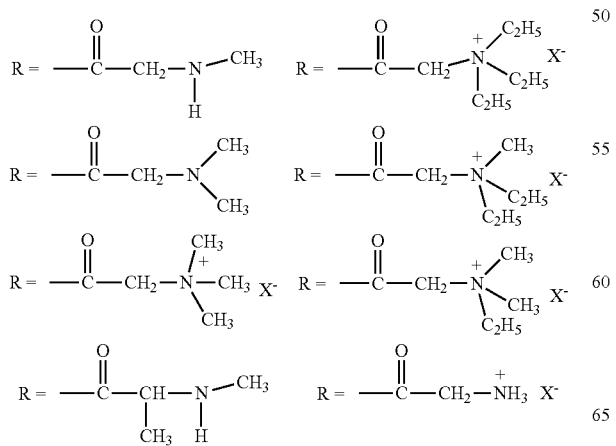
-continued
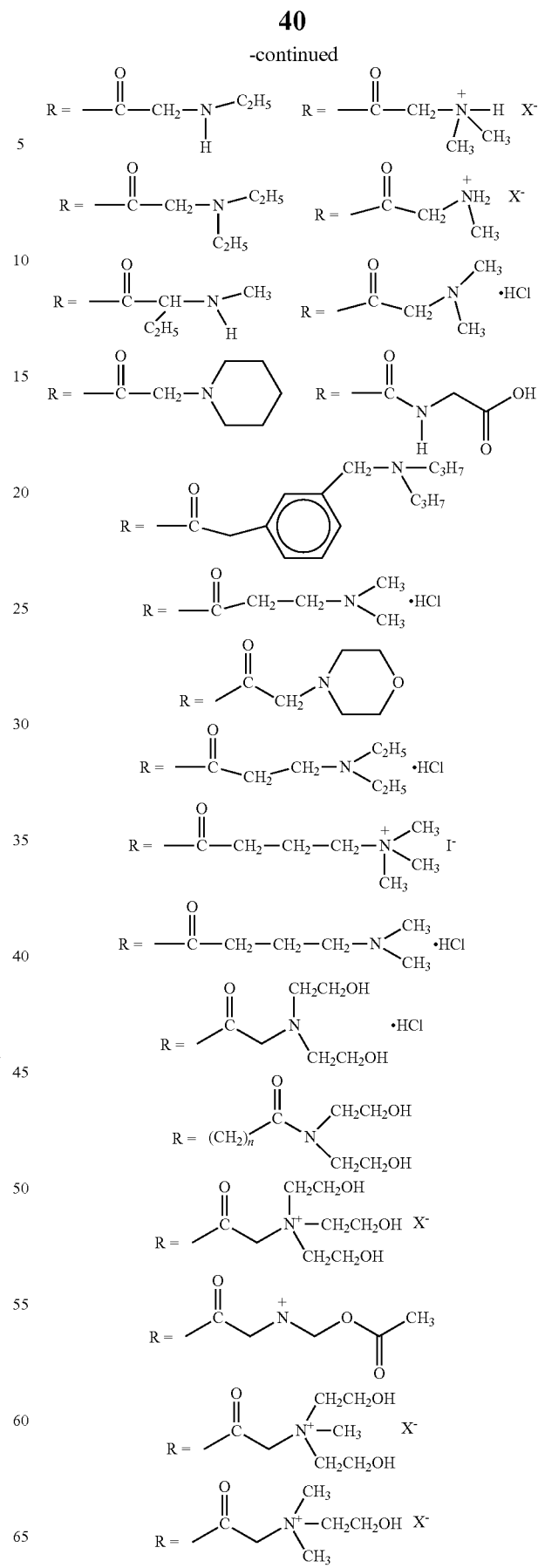

-continued

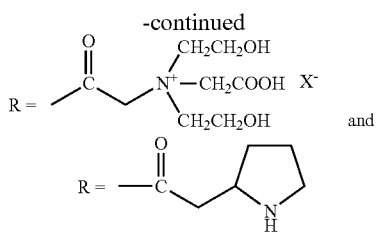

wherein X⁻ is anion pair of the corresponding cation;
wherein in compound 8,
$R_1$=OCH$_3$, $R_2$=OH, $R_3$=O-Glucose; or
$R_1$=OCH$_3$, $R_2$=H, $R_3$=O-Glucose; or
$R_1$=OCH$_3$, $R_2$=OH, $R_3$=OH; or
$R_1$=OCH$_3$, $R_2$=H, $R_3$=OH; or
$R_1$=OH, $R_2$=OH, $R_3$=O-Glucose; or
$R_1$=OH, $R_2$=OH, $R_3$=OH;
wherein in compound 12,
$R_1$, $R_2$, $R_3$, $R_4$, $R_5$, $R_6$, $R_7$, $R_8$ $R_9$, and $R_{10}$ are independently chosen from hydrogen, hydroxyl, hydrocarbyl, substituted hydrocarbyl, hydrocarbyloxy, substituted hydrocarbyloxy, or sulfoxy;
provided that at least one of the R groups is a hydroxyl or substituted hydroxyl group; and
provided that if compound 12 is monomeric, then compound 12 is other than resveratrol, wherein in compound 15,
$R_1$, $R_2$ and $R_3$, independently from one another, are each H or (C1-C3)alkyl; $R_4$ and $R_5$ are identical or different and are each hydrogen, linear or branched (C1-C5) alkyl, a prenyl group CH$_2$—CH═C(CH$_3$)$_2$, or a geranyl group CH$_2$—CH═C(CH$_3$)(CH$_2$)$_2$CH═C(CH$_3$)$_2$,
or $R_4$ and $R_1$, and independently $R_5$ and $R_2$, together with the atoms they are linked to, form one of the following groups:

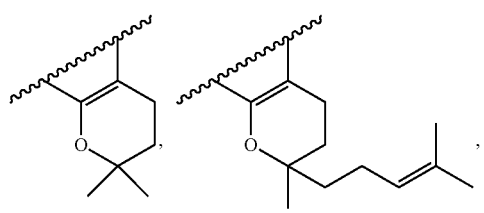

with the provisos that $R_4$ and $R_5$ are not both hydrogen and that when $R_1$=$R_2$=$R_3$=H, $R_4$ and $R_5$ are not a prenyl group and hydrogen, respectively,
wherein in compound 18, X, Y, and Z are either hydrogen or a protective group, provided that at least one of X, Y, and Z is the protective group.

16. The method of claim 15, wherein the reducing alpha-glucan or hydrolysis product of an alpha-glucan is selected from the group consisting of starch hydrolysis products, maltose, isomaltose, nigerose, melibiose, maltotriose, isomaltotriose, maltotetraose, maltodextrin, and icodextrin, or a mixture of two or more distinct alpha-glucans thereof.

17. The method of claim 15, wherein the reducing alpha-glucan is icodextrin.

18. A method for increasing the solubility of a stilbenoid, which is selected from the group consisting of resveratrol, a resveratrol derivative, piceatannol, pterostilbene and dihydro-resveratrol, in water, the method comprising the steps of:

dissolving a reducing alpha-glucan or hydrolysis product of an alpha-glucan in a predetermined concentration of ≥0.75% by weight (7.5 g/L) in a water-containing solution, wherein the reducing alpha-glucan or hydrolysis product of an alpha-glucan has a molecular weight between 350 D and 50 kD, and dissolving the stilbenoid in the water-containing solution that contains the dissolved reducing alpha-glucan or hydrolysis product of alpha-glucan to form an aqueous solution, wherein at least two times increase in solubility of the stilbenoid is detected in the presence of the predetermined concentration of the reducing alpha-glucan or hydrolysis product of an alpha-glucan;

wherein the resveratrol derivative is selected from one of piceid and the following compounds 1-9, 11, 12, 15, 16, 17 and 18:

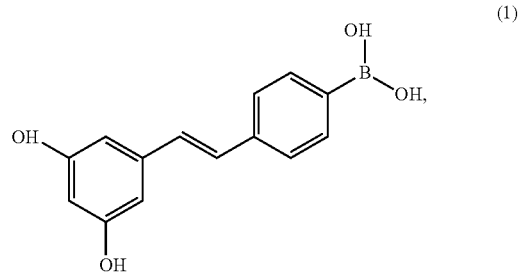

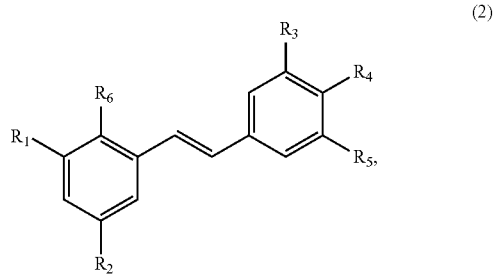

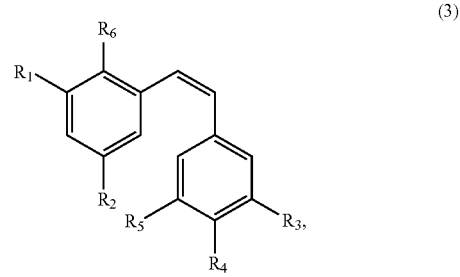

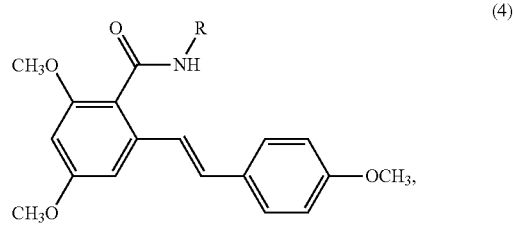

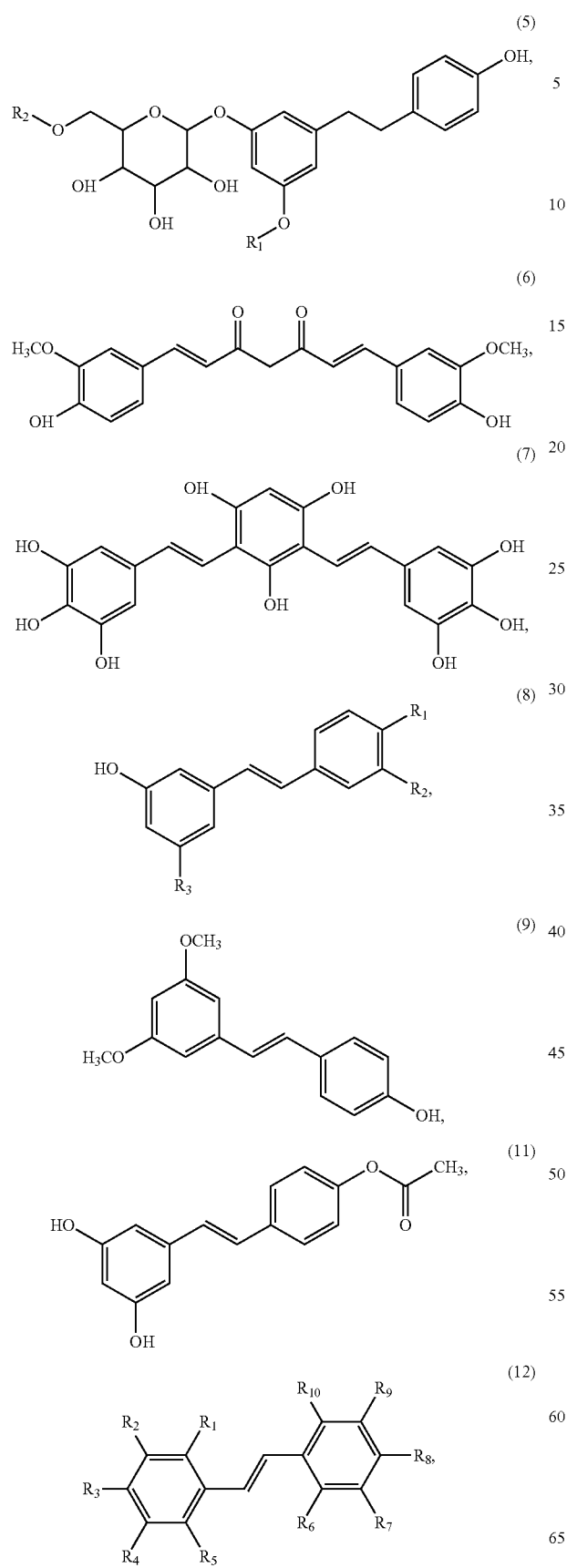
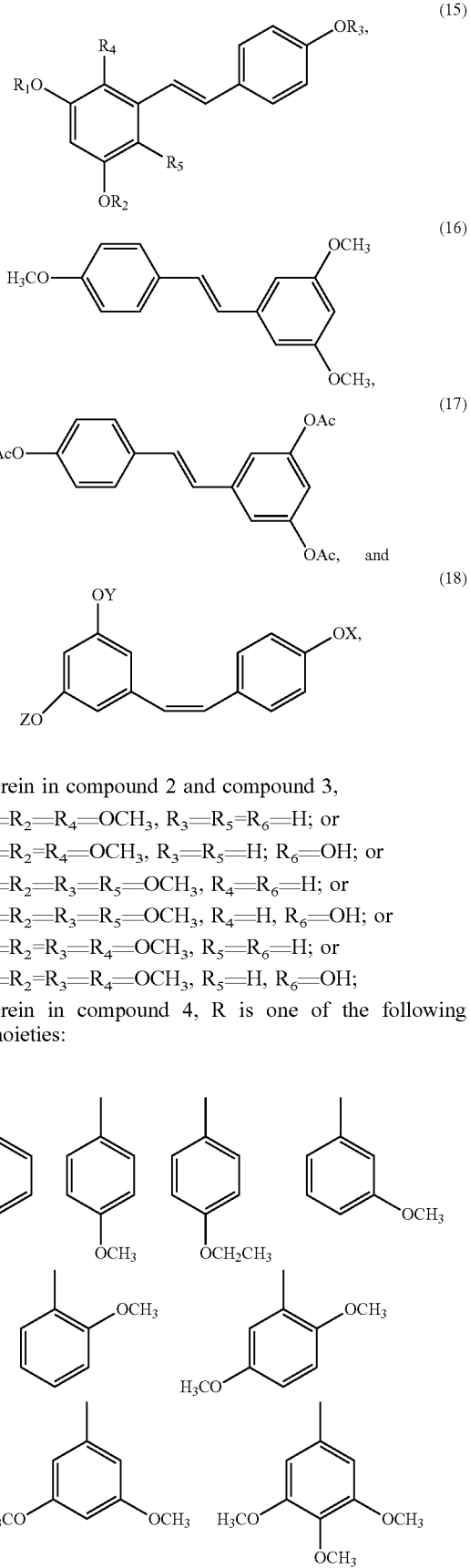
wherein in compound 2 and compound 3,
$R_1=R_2=R_4=OCH_3$, $R_3=R_5=R_6=H$; or
$R_1=R_2=R_4=OCH_3$, $R_3=R_5=H$; $R_6=OH$; or
$R_1=R_2=R_3=R_5=OCH_3$, $R_4=R_6=H$; or
$R_1=R_2=R_3=R_5=OCH_3$, $R_4=H$, $R_6=OH$; or
$R_1=R_2=R_3=R_4=OCH_3$, $R_5=R_6=H$; or
$R_1=R_2=R_3=R_4=OCH_3$, $R_5=H$, $R_6=OH$;
wherein in compound 4, R is one of the following moieties:
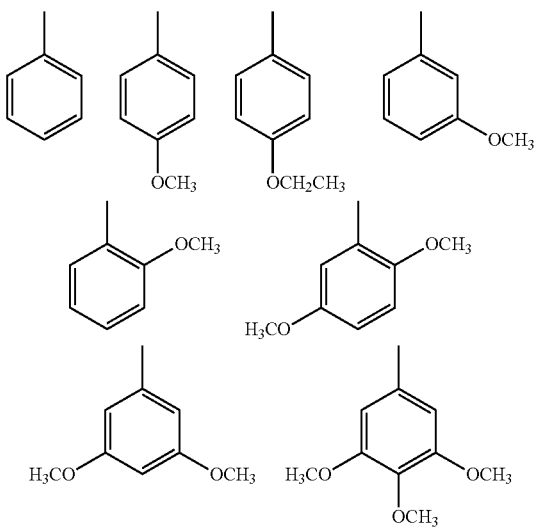

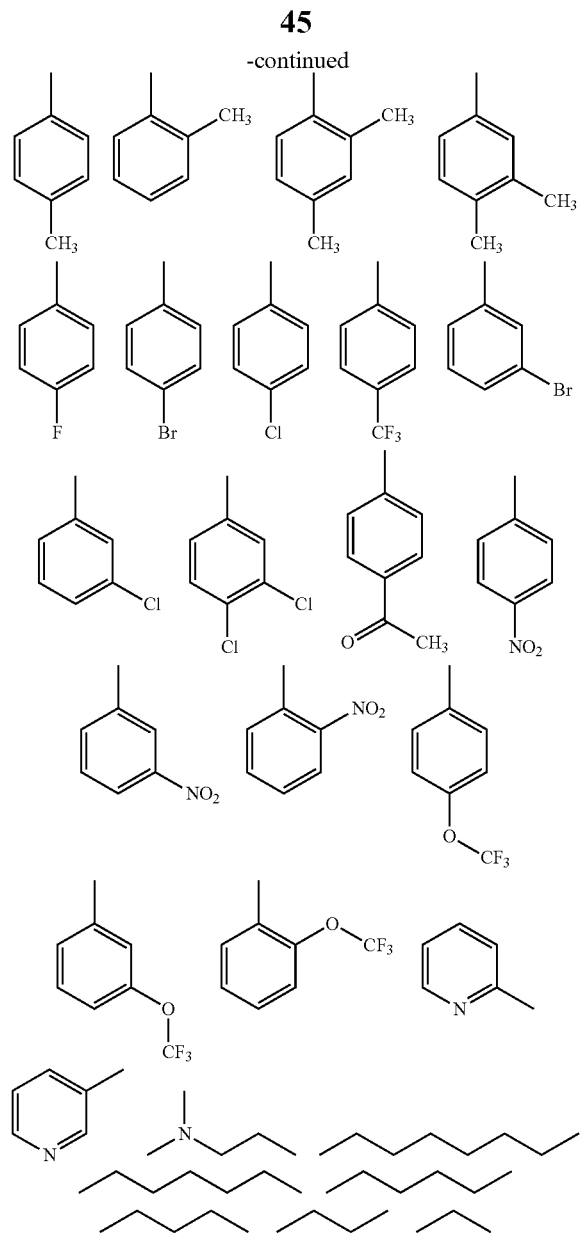
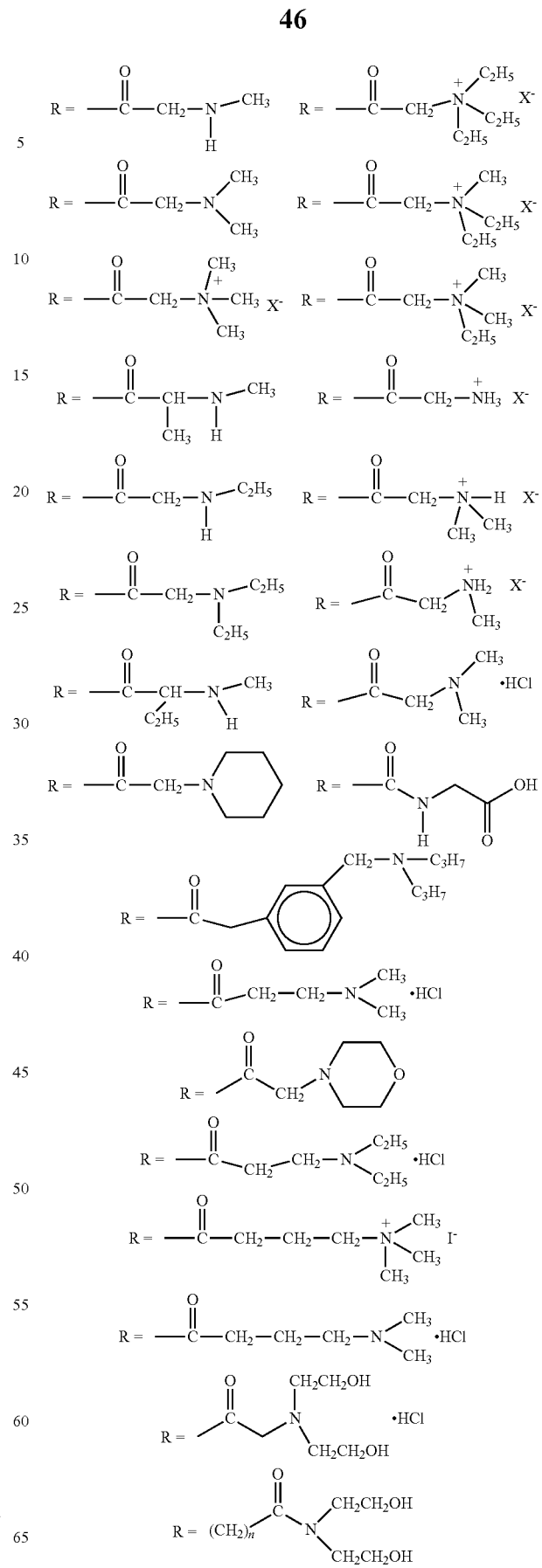
wherein in compound 5,
$R_1$ is hydrogen or a group of formula
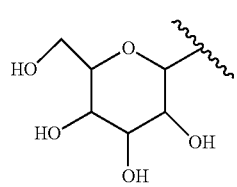 [SMILES: *C1OC(CO)C(O)C(O)C1O]
$R_2$ is hydrogen or forms together with the oxygen to which it is bound an acyl group (—OCO—$R_3$),
wherein $R_3$ is a C1-C22 alkyl group or a C2-C22 alkenyl group,
wherein, if $R_2$ is hydrogen $R_1$ is the formula defined in compound 5 above,
wherein in compound 6, R is one of the following moieties:

-continued

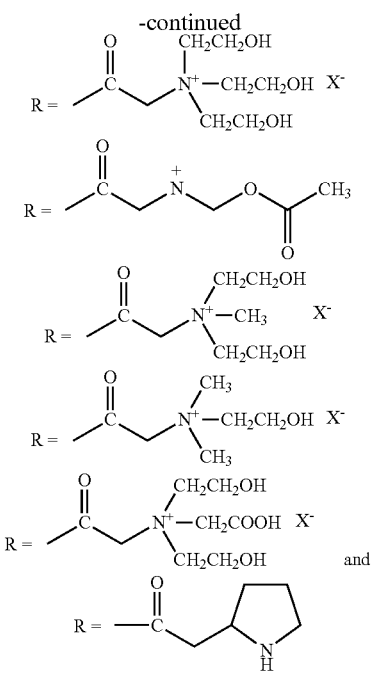

wherein X⁻ is anion pair of the corresponding cation;
wherein in compound 8,
$R_1$=OCH$_3$, $R_2$=OH, $R_3$=O-Glucose; or
$R_1$=OCH$_3$, $R_2$=H, $R_3$=O-Glucose; or
$R_1$=OCH$_3$, $R_2$=OH, $R_3$=OH; or
$R_1$=OCH$_3$, $R_2$=H, $R_3$=OH; or
$R_1$=OH, $R_2$=OH, $R_3$=O-Glucose; or
$R_1$=OH, $R_2$=OH, $R_3$=OH;
wherein in compound 12,
$R_1$, $R_2$, $R_3$, $R_4$, $R_5$, $R_6$, $R_7$, $R_8$ $R_9$, and $R_{10}$ are independently chosen from hydrogen, hydroxyl, hydrocarbyl, substituted hydrocarbyl, hydrocarbyloxy, substituted hydrocarbyloxy, or sulfoxy;
provided that at least one of the R groups is a hydroxyl or substituted hydroxyl group; and
provided that if compound 12 is monomeric, then compound 12 is other than resveratrol, wherein in compound 15,
$R_1$, $R_2$ and $R_3$, independently from one another, are each H or (C1-C3)alkyl; $R_4$ and $R_5$ are identical or different and are each hydrogen, linear or branched (C1-C5) alkyl, a prenyl group —CH$_2$—CH=C(CH$_3$)$_2$, or a geranyl group CH$_2$—CH=C(CH$_3$)(CH$_2$)$_2$CH=C(CH$_3$)$_2$,
or $R_4$ and $R_1$, and independently $R_5$ and $R_2$, together with the atoms they are linked to, form one of the following groups:

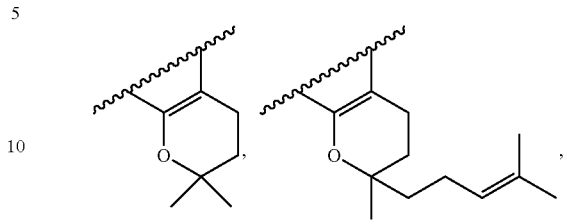

with the provisos that $R_4$ and $R_5$ are not both hydrogen and that when $R_1$=$R_2$=$R_3$=H, $R_4$ and $R_5$ are not a prenyl group and hydrogen, respectively,
wherein in compound 18, X, Y, and Z are either hydrogen or a protective group, provided that at least one of X, Y, and Z is the protective group; wherein the reducing alpha-glucan or hydrolysis product of an alpha-glucan is selected from the group consisting of starch hydrolysis products, maltose, isomaltose, nigerose, melibiose, maltotriose, isomaltotriose, maltotetraose, maltodextrin, and icodextrin, or a mixture of two or more distinct alpha-glucans thereof.

19. The method of claim 18, wherein the reducing alpha-glucan is icodextrin.

20. The method of claim 18, wherein the reducing alpha-glucan or hydrolysis product of an alpha-glucan is selected from the group consisting of starch hydrolysis products, maltose, isomaltose, nigerose, melibiose, maltotriose, isomaltotriose and maltoteraose, or a mixture of two or more distinct alpha-glucans thereof.

21. The method according to claim 18, wherein the stilbenoid is present in a concentration of 0.1 mg/L to 100 mg/L.

22. The method of claim 15, wherein the stilbenoid comprises resveratrol.

23. The method of claim 15, wherein the saccharide is maltose.

24. The method of claim 15, wherein the saccharide is maltodextrin.

25. The method of claim 18, wherein the stilbenoid comprises resveratrol.

26. The method of claim 18, wherein the hydrolysis product of an alpha-glucan is maltose.

27. The method of claim 18, wherein the hydrolysis product of an alpha-glucan is maltodextrin.

* * * * *